US012319960B2

(12) United States Patent
Davis et al.

(10) Patent No.: US 12,319,960 B2
(45) Date of Patent: Jun. 3, 2025

(54) NANOPORE VOLTAGE METHODS

(71) Applicant: Roche Sequencing Solutions, Inc., Pleasanton, CA (US)

(72) Inventors: Randall Davis, Pleasanton, CA (US); Markus Wallgren, Los Altos, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1062 days.

(21) Appl. No.: 16/341,250

(22) PCT Filed: Oct. 10, 2017

(86) PCT No.: PCT/EP2017/075782
§ 371 (c)(1),
(2) Date: Apr. 11, 2019

(87) PCT Pub. No.: WO2018/069302
PCT Pub. Date: Apr. 19, 2018

(65) Prior Publication Data
US 2019/0256904 A1    Aug. 22, 2019

Related U.S. Application Data

(60) Provisional application No. 62/407,257, filed on Oct. 12, 2016.

(51) Int. Cl.
*C12Q 1/6869* (2018.01)
*C12Q 1/6825* (2018.01)
*G01N 33/487* (2006.01)

(52) U.S. Cl.
CPC ......... *C12Q 1/6869* (2013.01); *C12Q 1/6825* (2013.01); *G01N 33/48721* (2013.01)

(58) Field of Classification Search
CPC ............. C12Q 1/6869; C12Q 1/6825; G01N 33/48721
See application file for complete search history.

(56) References Cited

U.S. PATENT DOCUMENTS

| | | | |
|---|---|---|---|
| 2013/0341192 A1* | 12/2013 | Dunbar | H03F 3/45076 204/601 |
| 2015/0011402 A1* | 1/2015 | Davis | C12Q 1/6869 506/2 |

(Continued)

FOREIGN PATENT DOCUMENTS

EP          1657539 A1    5/2006

OTHER PUBLICATIONS

Kim et al. (J Kim, G Wang, WB Dunbar, K Pedrotti, An integrated Patch-clamp amplifier for ultra-low current measurement on solid-state nanopore, 2010 International SoC Design Conference, 2010, 424-427, DOI: 10.1109/SOCDC.2010.5682879) (Year: 2010).*

(Continued)

*Primary Examiner* — Luan V Van
*Assistant Examiner* — Shizhi Qian
(74) *Attorney, Agent, or Firm* — Roche Sequencing Solutions, Inc.

(57) ABSTRACT

A method for sequencing a nucleic acid molecule includes providing a sequencing cell having a nanopore in a membrane that resides over a well, a first electrode at a bottom of the well, a second electrode in a chamber above the membrane, and an electrolyte in the well and the chamber. The first electrode is configured to facilitate non-Faradaic conduction of ionic current and forms a capacitance with ions in the electrolyte. A first voltage signal is applied across the first and second electrodes, thereby creating a force that moves a nucleic acid molecule in the sequence cell through the nanopore. The first voltage signal increases to compensate for changes in the capacitance at the first electrode during application of the first voltage signal. The method further includes determining signal values measured during the first voltage signal, which correspond to one or more nucleotides in the nucleic acid molecule.

13 Claims, 22 Drawing Sheets

(56) References Cited

U.S. PATENT DOCUMENTS

| | | | |
|---|---|---|---|
| 2015/0107996 A1* | 4/2015 | Chen | G01N 27/44743 204/451 |
| 2015/0109008 A1 | 4/2015 | Godin et al. | |
| 2015/0111779 A1* | 4/2015 | Davis | G01N 33/48721 506/9 |
| 2015/0153302 A1* | 6/2015 | Davis | G01N 27/3278 204/403.08 |
| 2015/0377856 A1* | 12/2015 | Dunbar | G01N 33/48728 204/452 |
| 2017/0091381 A1* | 3/2017 | Fernandez-Gomez | G01N 33/48721 |
| 2018/0045668 A1* | 2/2018 | Paik | G01N 21/553 |

OTHER PUBLICATIONS

Monitor Definition & Meaning, Merriam-Webster.com (Dec. 12, 2024), https://www.merriam-webster.com/dictionary/monitor#dictionary-entry-2.*

Monitor, v., Oxford English Dictionary (Dec. 12, 2024), https://www.oed.com/dictionary/monitor_v.tab=meaning_and_use#36265359.*

International search report and written opinion mailed on Feb. 26, 2018 in corresponding PCT application PCT/EP2017/075782 filed on Oct. 10, 2017.

* cited by examiner

NANOPORE VOLTAGE METHODS

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and properties of the molecule in the nanopore. In some cases, the molecule can be a particular tag attached to a particular nucleotide, thereby allowing detection of a nucleotide at a particular position of a nucleic acid. In other cases, the molecule can be threaded through the pore, allowing detection of a sequence of nucleotides of a nucleic acid. A voltage or other signal in a circuit including the nanopore can be measured (e.g., at an integrating capacitor) as a way of measuring the resistance of the molecule, thereby allowing detection of which molecule is in the nanopore.

A nanopore based sequencing chip may be used for DNA sequencing. A nanopore based sequencing chip can incorporate a large number of sensor cells configured as an array. For example, an array of one million cells may include 1000 rows by 1000 columns of cells.

The signals that are measured can vary from chip to chip and from cell to cell of a same chip due to manufacturing variability. Therefore, it can be difficult to determine the correct molecule, which may correspond to the correct nucleotide in a particular nucleic acid or other polymer in a cell. In addition, other time dependent non-idealities in the measured signals can lead to inaccuracies. For example, voltages of a sequencing cell may change over time. And, because these circuits employ biochemical circuit elements, e.g., lipid bilayers, nanopores, etc., the variability in the electrical characteristics can be much higher than for traditional semiconductor circuits. Further, sequencing processes are stochastic in nature, and thus variability can occur across a wide variety of systems, including sequencing devices not using nanopores.

Accordingly, improved characterization techniques are desired to improve the accuracy and stability of sequencing processes.

BRIEF SUMMARY

Various embodiments provide techniques and systems related to the measurement of a sequence of a nucleic acid in a sequencing cell, which may be in an array of sequencing cells (e.g., an array of nanopores on a chip).

In some embodiments of the invention, a method is provided for sequencing a nucleic acid molecule, for example, a single-stranded DNA molecule. The method can provide an applied voltage that is sufficient for sequencing the single-stranded nucleic acid over an extended period of time. A voltage with an increasing magnitude can be applied to the nanopore cell to maintain a nanopore voltage with enough magnitude to perform the sequencing throughout the duration of the applied voltage. The sequencing operation can also be made more efficient by allowing more of the nucleic acid molecule to be sequenced since the voltage can be applied for a longer duration. Increased accuracy can also be obtained as a result of the nanopore voltage being relatively constant (e.g., decreasing less than a threshold amount within a specified time period).

According to some embodiments, a method for sequencing a nucleic acid molecule includes providing a sequencing cell. The sequencing cell can include a nanopore in a membrane that resides over a well, a first electrode at a bottom of the well, a second electrode in a chamber above the membrane, and an electrolyte in the well and the chamber. The first electrode can be configured to facilitate non-Faradaic conduction of ionic current and forms a capacitance with ions in the electrolyte. The method can also include applying a first voltage signal across the first electrode and the second electrode, thereby creating a force that moves a nucleic acid molecule in the sequence cell through the nanopore. The first voltage signal can be configured to increase at a first rate that compensates for a change in the capacitance at the first electrode during application of the first voltage signal. The method can further include determining a first set of signal values measured during the first voltage signal, the first set of signal values corresponding to one or more nucleotides in the nucleic acid molecule.

According to alternative embodiments, a method for sequencing a nucleic acid molecule can include providing a sequencing cell. The sequencing cell can have a nanopore in a membrane that resides over a well, a first electrode at a bottom of the well, a second electrode in a chamber above the membrane, and an electrolyte in the well and the chamber. A first voltage signal can be applied across the first electrode and the second electrode, thereby creating a force that moves a nucleic acid molecule in the sequence cell through the nanopore, and a first set of one or more signal values measured during the first voltage signal can be determined. The first set of signal values can correspond to one or more nucleotides in the nucleic acid molecule. The method can include monitoring a magnitude of nanopore voltage across the nanopore relative to a preset reference voltage. Upon determining that the magnitude of nanopore voltage is below the preset reference voltage, the magnitude of the first voltage signal can be increased to a second voltage such that the nanopore voltage is equal to or higher than the preset reference voltage. A second set of one or more signal values can be measured. The second set of signal values can correspond to one or more nucleotides in the nucleic acid molecule.

According to other embodiments, a method for sequencing a nucleic acid molecule can include providing a sequencing cell. The sequencing cell can have a nanopore in a membrane that resides over a well, a first electrode at a bottom of the well, a second electrode in a chamber above the membrane, and an electrolyte in the well and the chamber. The method can include applying a first voltage signal across the first electrode and the second electrode, thereby creating a force that moves a nucleic acid molecule in the sequence cell through the nanopore. The first voltage signal can include a plurality of voltage pulse signals superimposed over a base voltage. The method can also include determining a first set of signal values measured during the first voltage signal. The first set of signal values can correspond to one or more nucleotides in the nucleic acid molecule.

Other embodiments are directed to systems and computer readable media associated with methods described herein, as well as instruments comprising such computer readable media.

TERMS

Figure 1:
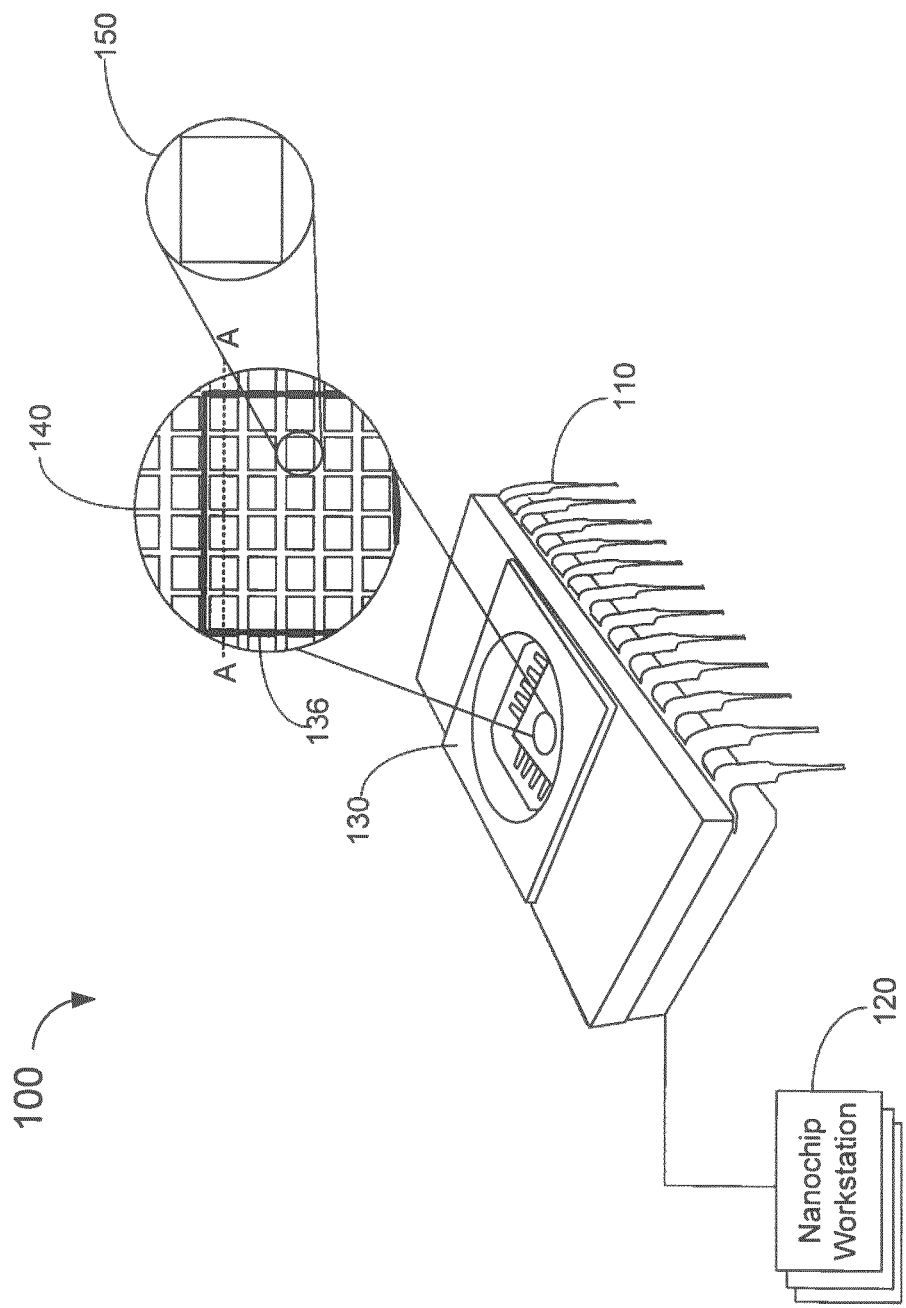
FIG. 1 is a top view of an embodiment of a nanopore sensor chip having an array of nanopore cells according to embodiments of the present invention.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

A "nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

A "polymerase" may refer to an enzyme that performs template-directed synthesis of polynucleotides. The term encompasses both a full length polypeptide and a domain that has polymerase activity. DNA polymerases are well-known to those skilled in the art, and include, but are not limited to, DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. In some implementations, a nanopore may be a protein.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "tag" may refer to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

The term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different. The bright periods and the dark periods can correspond to different portions of an alternating signal relative to a reference voltage.

The term "signal value" may refer to a value of the sequencing signal output from a sequencing cell. According to certain embodiments, the sequencing signal may be an electrical signal that is measured and/or output from a point in a circuit of one or more sequencing cells, e.g., the signal value may be (or represent) a voltage or a current. The signal value may represent the results of a direct measurement of voltage and/or current and/or may represent an indirect measurement, e.g., the signal value may be a measured duration of time for which it takes a voltage or current to reach a specified value. A signal value may represent any measurable quantity that correlates with the resistivity of a nanopore and from which the resistivity and/or conductance of the nanopore (threaded and/or unthreaded) may be derived. As another example, the signal value may correspond to a light intensity, e.g., from a fluorophore attached to a nucleotide being catalyzed to a nucleic acid with a polymerase.

The term "bulky structure" may refer to a nucleotide structure formed from a pre-bulky structure in a ss test DNA molecule. A pre-bulky structure, as used herein, is an oligonucleotide structure in a DNA molecule that can form a bulky structure under certain conditions. The pre-bulky structure can be a ss DNA or a ds DNA. The bulky structure stalls the test DNA molecule in a nanopore at a working condition until the working condition is changed to another condition wherein the bulky structure is converted to the pre-bulky structure or other structures that cannot stall the test DNA molecule any more. Examples of bulky structures include, without limitation, 2-D and 3-D structures such as DNA duplex structures, DNA hairpin structures, multi-hairpin structures and multi-arm structures.

The term "speed bump" may refer to an oligonucleotide molecule that forms a complex with a binding segment of a test DNA molecule. When the test DNA molecule goes through a nanopore under an electric potential, the complex formed between the speed bump and the binding segment stalls the test DNA molecule in the nanopore for a dwelling time long enough for the nanopore detector to obtain structure information of the test DNA molecule. After the dwelling time, the complex dissociates and the test DNA molecule moves forward through the nanopore.

DETAILED DESCRIPTION

Ideally, individual nucleotides of a single-stranded (ss) nucleic acid, such as DNA, passing through a nanopore will uniquely modulate an ionic current flowing through the nanopore, allowing the recording of the current to provide DNA sequence information. However, a common challenge to nanopore sequencing is that the ss test DNA translocation is rapid, and the electrical signals obtained cannot be resolved for reliable DNA sequencing. DNA duplex sections have been used to slow translocation of a ss test DNA to provide more resolvable electrical signals. In a non-Faradaic sequencing cell, the nanopore voltage has been observed to drop below a usable voltage needed to move the ss DNA through the nanopore, resulting in inefficient sequencing operation.

In the sections below, introductory sections describe various biological processes and electrical devices that may be used in various embodiments. Sequencing of single strand (ss) DNA is a non-Faradaic cell is described. The loss of nanopore voltage due to the capacitive nature of the non-Faradaic cell is described. Various methods for maintaining useful nanopore voltage are then described. As a result, sequencing of ss DNA can be carried out over extended periods of time, improving the efficiency of the sequencing operation.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid. In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
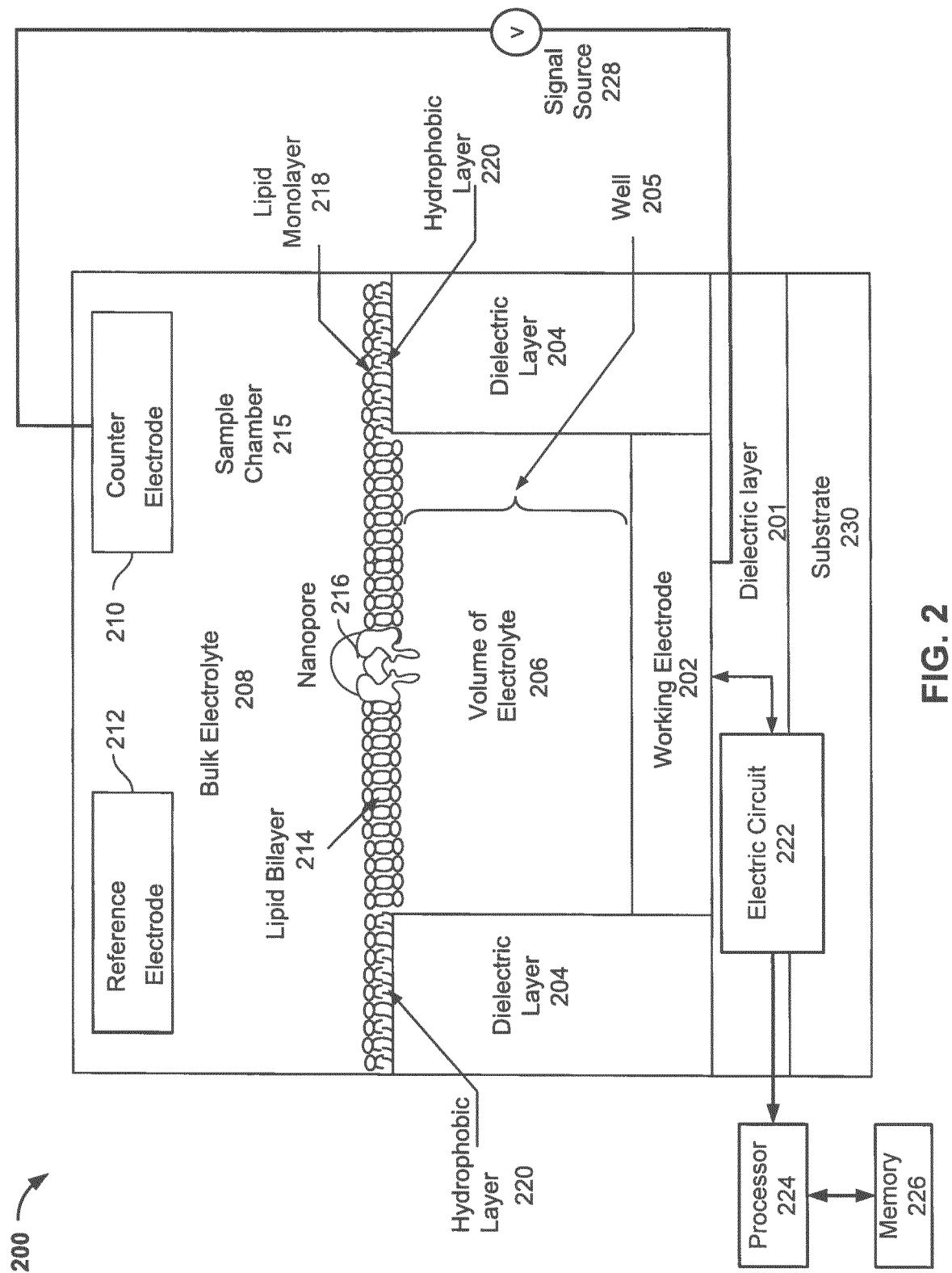
FIG. 2 illustrates an embodiment of a nanopore cell in a nanopore sensor chip that can be used to characterize a polynucleotide or a polypeptide according to embodiments of the present invention.

FIG. 2 illustrates an embodiment of a nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. A dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometers (nm).

Well 205 formed by walls of the dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethyleneglycol)-350]; 1,2-dipalmitoyl-sn-glycero-3-phosphoethanolamine-N-[methoxy(polyethyleneglycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethyleneglycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

Figure 3:
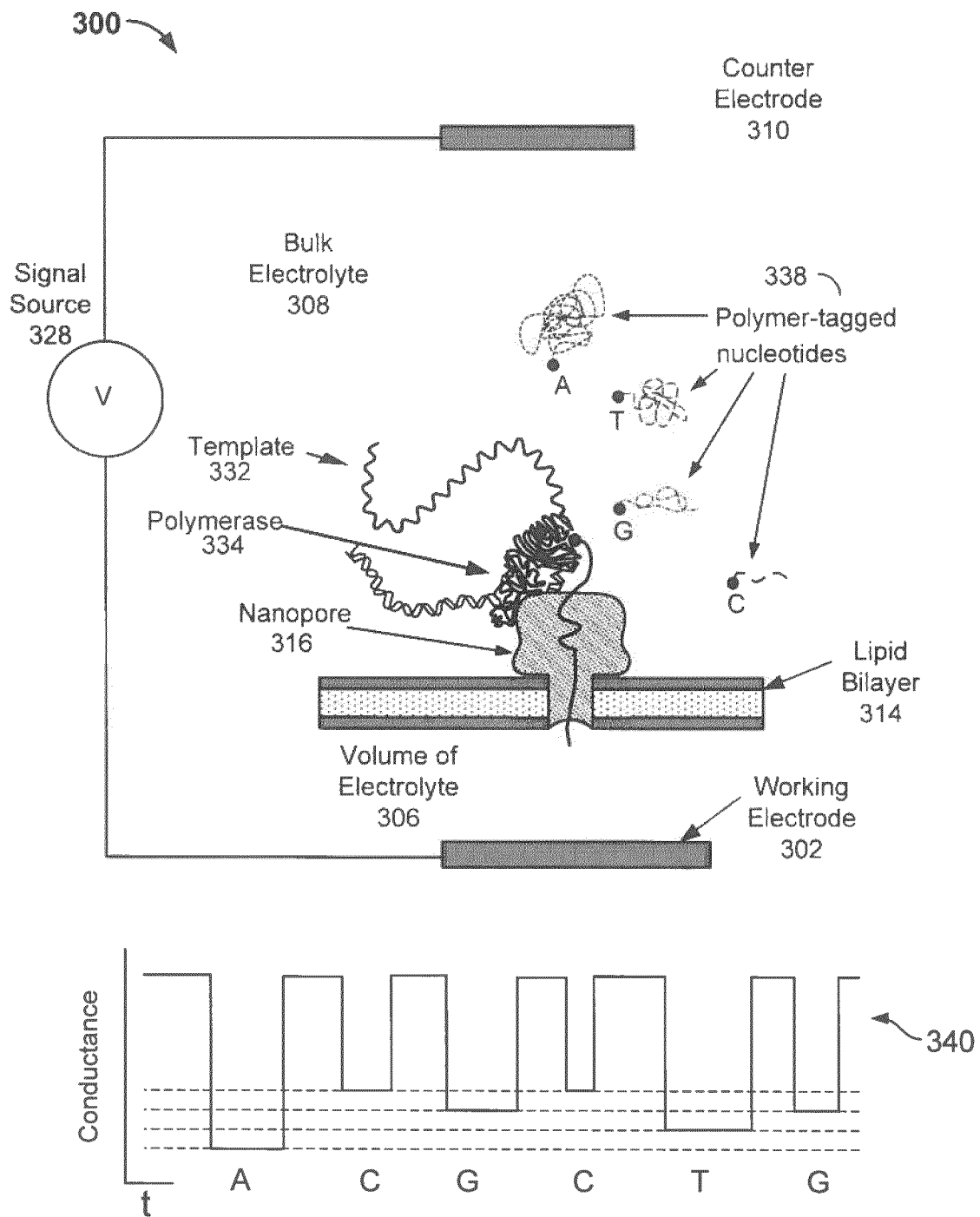
FIG. 3 illustrates an embodiment of a nanopore cell performing nucleotide sequencing using a nanopore-based sequencing-by-synthesis (Nano-SBS) technique according to embodiments of the present invention.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly bound with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10,000 milliseconds. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver) are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width and total area of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
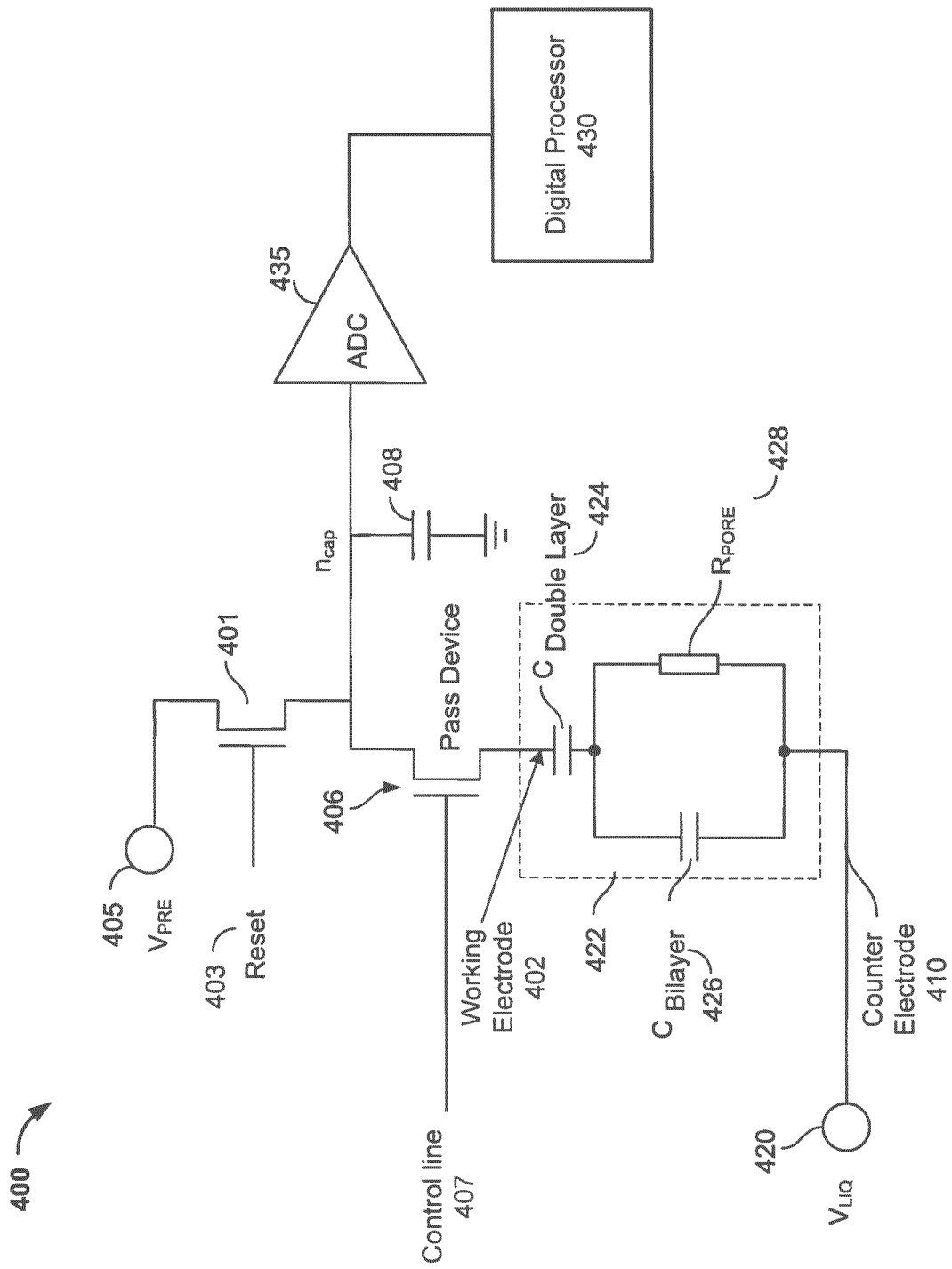
FIG. 4 illustrates an electric circuit in a nanopore cell according to embodiments of the present invention.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 410 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 410 and the lipid bilayer (e.g., lipid bilayer 214) modeled by a large capacitor 426, such as, for example, 100 μF or larger.

FIG. 4 also shows an electrical model 422 representing the electrical properties of a working electrode 402 (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 402 and well 205. Working electrode 402 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Circuitry 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to the reference voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 410 may be at a level higher than the potential of working electrode 402 (and integrating capacitor 408), or vice versa. For example, during a positive phase of a square wave from voltage source $V_{LIQ}$ (e.g., the bright or dark period of the AC voltage source signal cycle), the potential of counter electrode 410 is at a level higher than the potential of working electrode 402.

During a negative phase of the square wave from voltage source $V_{LIQ}$ (e.g., the dark or bright period of the AC voltage source signal cycle), the potential of counter electrode 410 is at a level lower than the potential of working electrode 402. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 410 and working electrode 402. In other embodiments, the charging and discharging may occur in dark periods and bright periods, respectively.

Integrating capacitor 408 may be charged or discharged for a fixed period of time, depending on the sampling rate of an analog-to-digital converter (ADC) 435, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 435 at the end of the integration period. A particular voltage level would correspond to a particular tag species in the nanopore, and thus correspond to the nucleotide at a current position on the template.

After being sampled by ADC 435, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 435 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau=RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MΩ to 20 GΩ. In some embodiments, the resistance associated with the nanopore in a state where a tag is inside the barrel of the nanopore may be within the range of 200 MΩ to 40 GΩ. In other embodiments, integrating capacitor 408 may be omitted, as the voltage leading to ADC 435 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 435 at time t1, and then the voltage is measured again by ADC 435 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408

($n_{cap}$) or capacitor 426 ($C_{Bilayer}$)) can be sampled and converted by the ADC (e.g., ADC 435) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Periods

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotide) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is pre-charged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
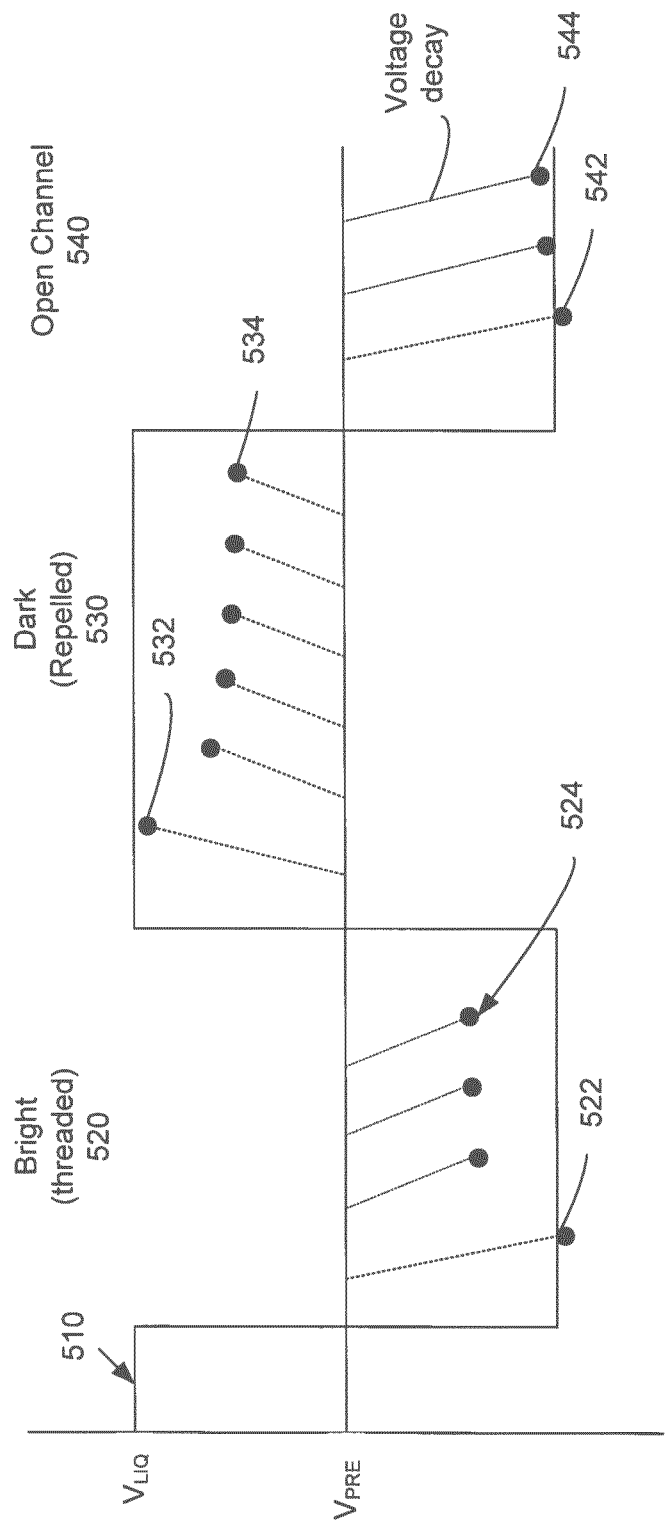
FIG. 5 shows example data points captured from a nanopore cell during bright periods (portions) and dark periods (portions) of AC cycles according to embodiments of the present invention.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

Further details regarding measurements can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

4. Normalization and Base Calling

For each usable nanopore cell of the nanopore sensor chip, a production mode can be run to sequence nucleic acids. The ADC output data captured during the sequencing can be normalized to provide greater accuracy. Normalization can account for offset effects, such as cycle shape, gain drift, charge injection offset, and baseline shift. In some implementations, the signal values of a bright period cycle corresponding to a threading event can be flattened so that a single signal value is obtained for the cycle (e.g., an average) or adjustments can be made to the measured signal to reduce the intra-cycle decay (a type of cycle shape effect). Gain drift generally scales entire signal and changes on the order to hundreds to thousands of seconds. As examples, gain drift can be triggered by changes in solution (pore resistance) or changes in bilayer capacitance. The baseline shift occurs with a timescale of ~100 ms, and relates to a voltage offset at the working electrode. The baseline shift can be driven by changes in an effective rectification ratio from threading as a result of a need to maintain charge balance in the sequencing cell from the bright period to the dark period.

After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Example methods of determining bases of a nucleic acid based on signal measurements are provided below. Although the examples may use voltage measurements for illustration, the example techniques equally apply to other signal measurements, such as current measurements.

III. Sequencing of Single Strand DNA

In the systems and methods for sequencing a nucleic acid samples described above, an individual tagged nucleotide of the tagged nucleotides can be incorporated into a growing strand complementary to a single stranded nucleic acid molecule derived from the nucleic acid sample. With the aid of the nanopore, a tag associated with the individual tagged nucleotide can be detected during incorporation of the individual tagged nucleotide.

In embodiments described below, a single-stranded (ss) nucleic acid, such as DNA, with certain modifications such as speed bumps or gated hinges, is moved through a nanopore. Individual nucleotides of the ss nucleic acid passing through a nanopore will uniquely modulate an ionic current flowing through the nanopore, allowing the recording of the current to provide DNA sequence information.

A. Nanopore Sequencing Cell for Single Strand DNA Through Nanopore

Figure 6:
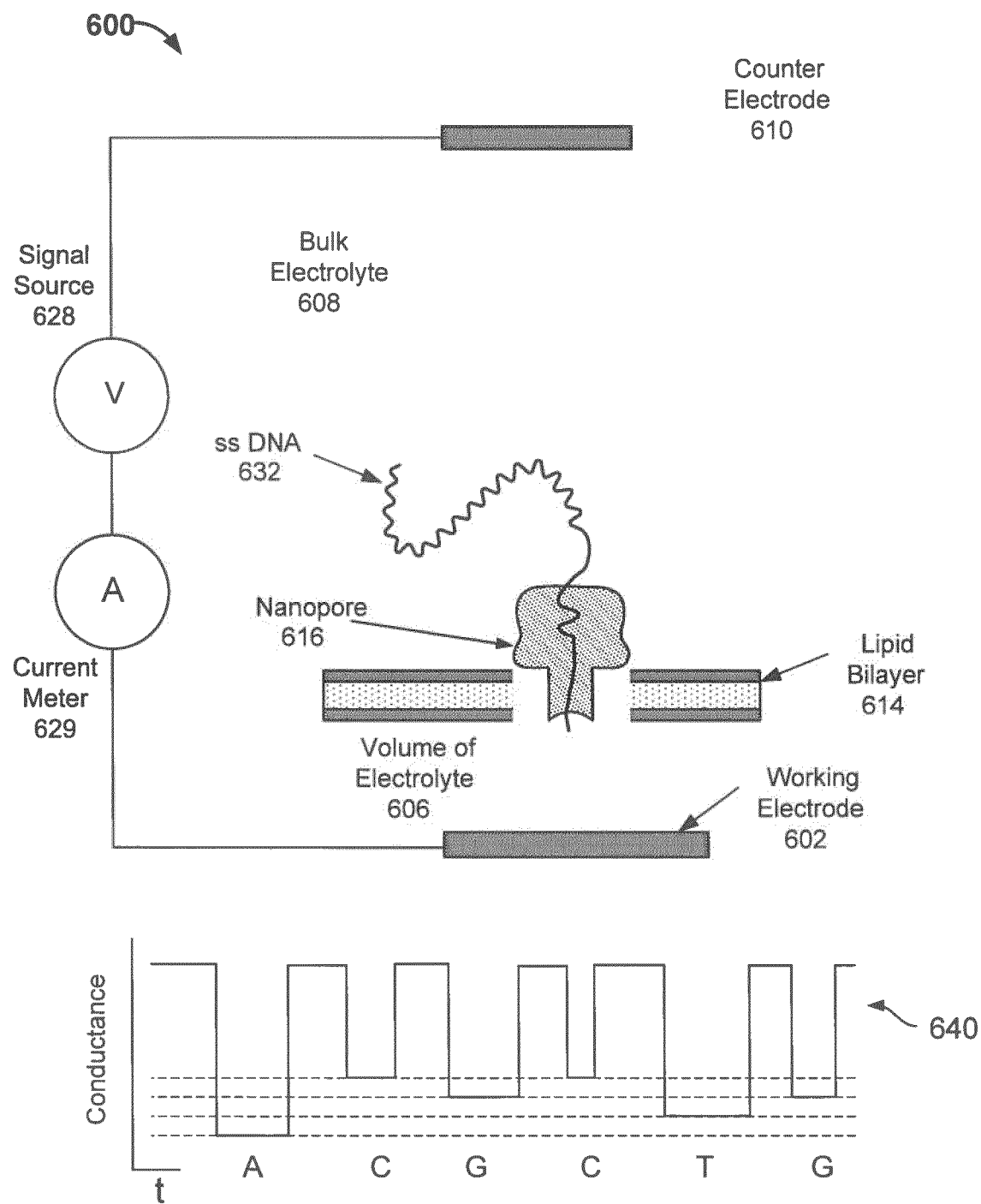
FIG. 6 illustrates an embodiment of a nanopore cell in a nanopore sensor chip that can be used to characterize a single strand DNA according to embodiments of the present invention.

FIG. 6 illustrates a nanopore cell 600 for performing single strand nucleotide sequencing according to embodiments of the invention. Nanopore cell 600 has a similar cell structure as nanopore cell 300 of FIG. 3. For example, nanopore cell 600 has a sample chamber that has bulk electrolyte 608, a nanopore 616 disposed in a lipid bilayer 614, and a volume of electrolyte 606 in a well below the nanopore. Nanopore cell 600 also has a working electrode 602 and a counter electrode 610 for receiving an applied voltage V from a signal source 628.

A single strand nucleotide acid molecule 632 (or another analyte of interest) to be sequenced may be introduced into bulk electrolyte 608 in the sample chamber of nanopore cell 600. The single strand nucleotide acid molecule 632 may be pulled into the nanopore by an electrical force generated in the presence of an electric field generated by the voltage applied across lipid bilayer 614 and/or nanopore 616. A current meter 629 is used to measure a current flow through the nanopore cell. Alternatively, if a current source is used to provide the electrical force, a voltmeter is used for the measurement. The portion of the single strand nucleotide acid molecule 632 held in the barrel of nanopore 616 may generate a unique ionic blockade signal 640 due to the distinct chemical structure and/or size of the base in that portion, thereby electronically identifying the base in the molecule. The base can be one of four different types: A, T, G, or C, as represented by the conductance signal 640 shown in FIG. 6

A conductance (or equivalently the resistance) of the nanopore, including the loaded (threaded) single strand nucleotide acid molecule, can be measured via a current passing through the nanopore, thereby providing an identification of the tag species and thus the nucleotide at the current position. In some embodiments, a direct current (DC) signal can be applied to the nanopore cell (e.g., so that the direction at which the molecule moves through the nanopore is not reversed). However, operating a nanopore sensor for long periods of time using a direct current can change the capacitive properties of the cell, unbalance the ion concentrations across the nanopore, and have other undesirable effects that can affect the lifetime of the nanopore cell. Applying an alternating current (AC) waveform can reduce these undesirable effects and have certain advantages as described below. Suitable conditions for measuring ionic currents passing through the nanopores can be similar to those described above in connection with FIGS. 1-5.

Figure 7:
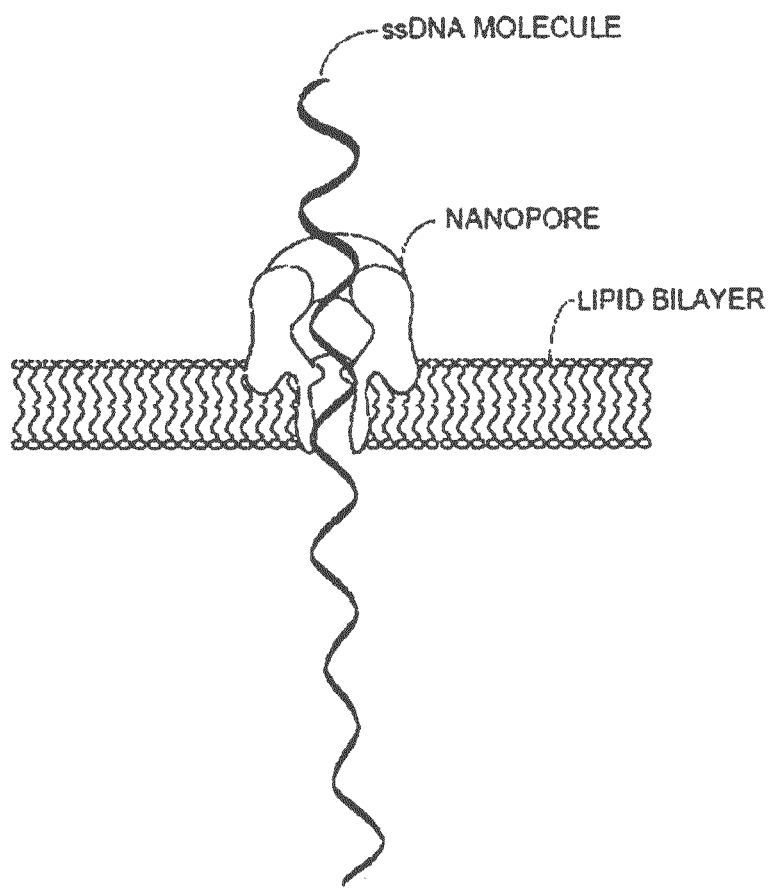
FIG. 7 illustrates an embodiment of part of a nanopore cell in a nanopore sensor chip with a single strand DNA passing through a nanopore according to embodiments of the present invention.

FIG. 7 illustrates part of a nanopore cell in a nanopore sensor chip with a single strand DNA passing through the nanopore according to embodiments of the invention. As illustrated in FIG. 7, a single-stranded (ss) DNA molecule can go through a nanopore under an applied electric potential. A set of electrical signals corresponding to the brief blockages of ion flow through the nanopore by the ss test DNA molecule can be detected as the ss test DNA molecule is threaded through the nanopore. In the absence of speed bumps or bulky structures, the ss test DNA molecule encounters little resistance and travels through the nanopore too quickly for electrical signals to be reliably recorded for sequencing of the ss test DNA.

Figure 8:
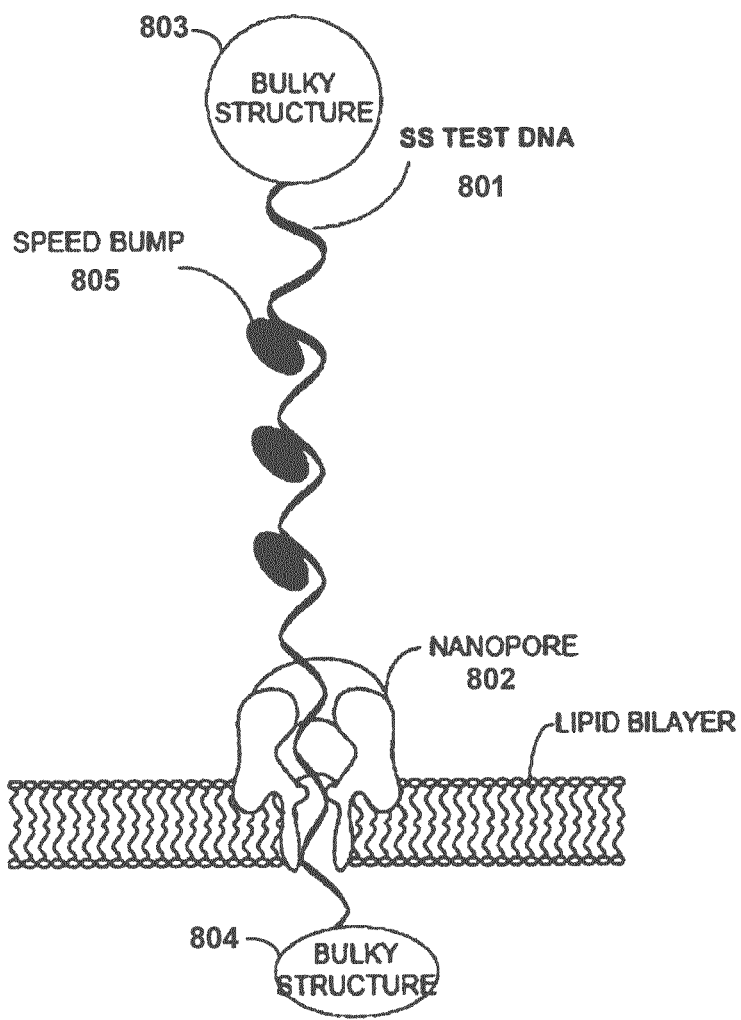
FIG. 8 illustrates an embodiment of part of a nanopore cell in a nanopore sensor chip with a single strand DNA having speed bumps passing through a nanopore according to embodiments of the present invention.
Figure 9:
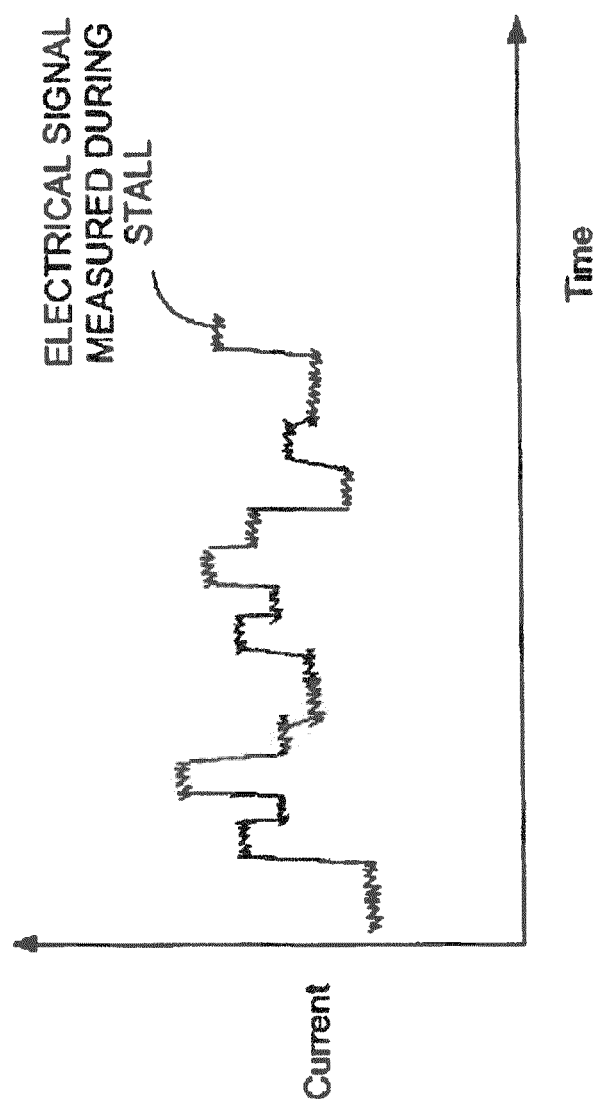
FIG. 9 illustrates an example of electrical signals measured in an embodiment of a nanopore cell in a nanopore sensor chip with a single strand DNA passing through a nanopore according to embodiments of the present invention.

FIGS. 8 and 9 are related to a method of using nanopores to obtain sequence information of sample DNAs in single strand (ss) test DNAs. The method includes using speed bumps to stall the ss test nucleic acids in the nanopores to obtain sequence information of nucleotides of the sample nucleic acids near the location of the speed bumps, and to construct the whole sequences of the sample DNAs. The method also relates to identification and/or isolation of test DNAs having desired sequence(s) using nanopore detectors facilitated by speed bumps. More details are described in U.S. Patent Application No. 20150011402, filed Aug. 28, 2014, the content of which is incorporated by reference in its entirety. For example, the nucleic acids can have synthesized sequences inserted between the naturally occurring nucleotides. Such synthesized sequences can allow a larger spacing between the speed bumps so a speed bump can be attached for allowing sequencing of each nucleotide. In another example, the synthesized sequences can be detected themselves, e.g., as a proxy for a particular nucleotide.

FIG. 8 illustrates part of a nanopore cell in a nanopore sensor chip with a single strand DNA having speed bumps passing through the nanopore according to embodiments of the invention. FIG. 8 illustrates a ss test DNA 801 trapped in a nanopore 802 by two bulky structures 803 and 804. The ss test DNA with bulky structures formed on both ends is locked in a nanopore and forms speed bump-test DNA complex with multiple speed bumps 805. In some embodiments, the bulky structures (BS) can be a hairpin structure formed at one end of the ss test DNA by wrapping the trailing end of the ss test DNA upon itself. A speed bump can be an oligonucleotide molecule that forms a complex with a binding segment of a test DNA molecule. The ss test DNA can contact a random speed bump pool with the ss test DNA to form a speed bump-ss test DNA complex.

The nanopore detection is carried out so that one or more shorter DNA duplex sections can be formed between speed bumps and the ss test DNA (speed bump-test DNA duplex segments). The speed bump-test DNA duplex segment stalls the ss test DNA for a sufficient dwelling time to obtain sequence information of the ss test DNA segment in front of the speed bump-test DNA duplex segment and the first basepair of the speed bump-test DNA duplex segment in the flow direction of the ss test DNA. Then the speed bump-test DNA duplex segment dissociate and the ss test DNA moves forward through the nanopore until stalled by another speed bump-test DNA duplex segment or stopped by a bulky structure on one end of the ss test DNA. Once the ss test DNA reaches one end, the electric potential can be optionally at a reduced value or a reversed polarity to move the ss test DNA to a reversed direction and repeat the process as desired.

A set of electrical signals of the ss test DNA are obtained each time the ss test DNA is stalled by a speed bump-test DNA duplex segment in the nanopore for a dwelling time, and then the speed bump-test DNA duplex segment dissociates and the ss test DNA moves forward until stalled by the next speed bump-test DNA duplex segment. This stall-detect-disassociate-stall process is repeated until the ss test DNA is stopped by the bulky structure of one end.

FIG. 9 illustrates an example of electrical signals measured in a nanopore cell in a nanopore sensor chip with a single strand DNA passing through the nanopore according to embodiments of the invention. For ease of illustration, the electrical signals are simplified to show only the levels related to the bases and not any speed bumps. The speed bump-identifier duplex segment stalls the ss test DNA and a set of electrical signals are obtained, where relatively flat levels are shown during a stall. These signals can be characterized to show presence of the identifier or to identify the sequence of the segment before the identifier in the flow direction of the ss test DNA.

Figure 20:
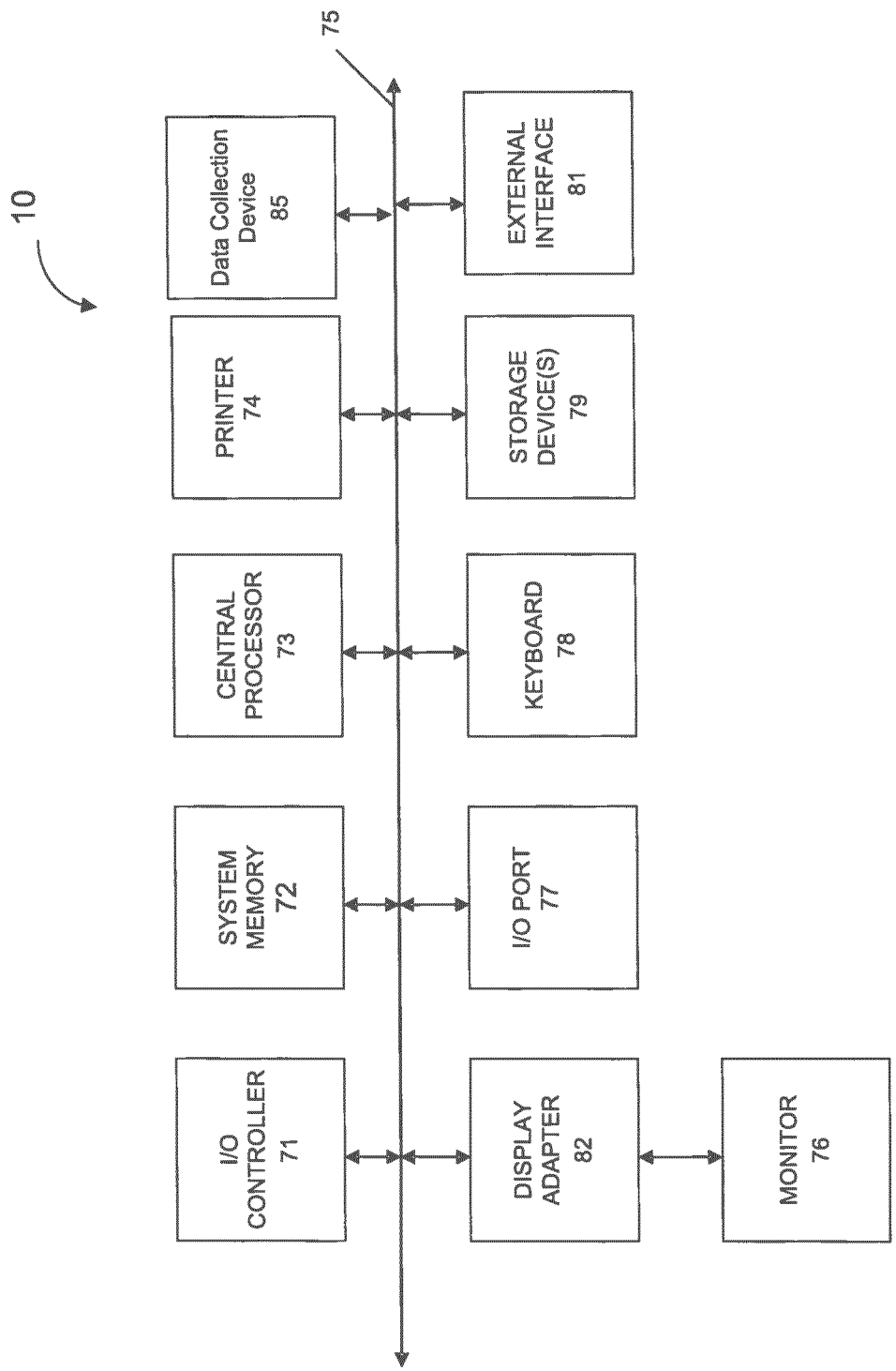
FIG. 20 shows a block diagram of an example computer system usable with the system and methods described herein according to embodiments of the present invention.

The speed bumps illustrate one way to stall the passage of a nucleic acid molecule through a nanopore to allow electrical signal measurement for sequencing. The speed bumps can take various forms and may be unidirectional, in that they can pass through the nanopore in the forward direction (although after hesitation), but not pass through the nanopore in an opposite direction (e.g., during a negative portion of an AC cycle). With reference to FIG. 2 and according to some embodiments, the lipid bilayer 214 (comprising nanopore 216) is further defined as having a trans side and a cis side. In one embodiment, the trans side is well 205 comprising the volume of electrolyte 206. In another embodiment, the cis side is sample chamber 215 comprising the bulk electrolyte 208. In one embodiment, the unidirectional speed bump(s) comprises a single stranded nucleic acid connected to the backbone of the nucleic acid molecule that will pass through the nanopore. In another embodiment, the single stranded nucleic acid is connected to the backbone of the nucleic acid molecule (i) at an angle that points away from the nanopore, or (ii) in such a way that it is pointed towards the cis side (and away from the trans side) of the lipid bilayer 214 (comprising nanopore 216) while the nucleic acid molecule passes through the nanopore. The single stranded nucleic acid may be barbed as shown in FIG. 20 or FIG. 32 of U.S. Pat. No. 9,605,309 (incorporated herein by reference in its entirety). In another embodiment, the unidirectional speed bump(s) comprises a hinged gate attached to the nucleic acid molecule that is thin enough to pass through the nanopore when the gate is aligned with the nucleic acid molecule in a first direction, but not in a second direction. In one embodiment, the hinged gate comprises a first segment which is narrower than a second segment, wherein the second segment comprises a width that is smaller than the narrowest opening of the nanopore. In one other embodiment, the hinged gate further comprises a polymer chain having a first end and a second end. In other embodiments, the first end is attached to the nucleic acid molecule in a position that is adjacent to the second segment and the second end is not attached to the nucleic acid molecule. The nucleic acid molecule having a gated hinge is capable of being threaded through a nanopore in a first direction where the polymer chain aligns adjacent to the second segment. In some cases, the tag molecule is not capable of being threaded through the nanopore in a second direction where the polymer chain does not align adjacent to the second segment. In one embodiment, the second direction is opposite the first direction. The hinged gate may be as depicted in FIG. 31 of U.S. Pat. No. 9,605,309 (incorporated herein by reference in its entirety).

B. Limitations of Non-Faradaic Cell Caused by Nanopore Voltage Drop

As described above, FIG. 6 illustrates an embodiment of a cell in a nanopore based sequencing chip configured for non-faradaic and capacitively coupled measurements. The cell includes an analog measurement circuit (not shown) for making non-faradaic and capacitively coupled measurements. The measurements can be converted to digital information and transmitted out of the cell. In some embodiments, the transmission data rate can be on the order of gigabits per second. In some embodiments, a field programmable gate array (FPGA) or an application-specific integrated circuit (ASIC) receives the transmitted data, processes the data, and forwards the data to a computer.

In non-faradaic conduction, no chemical reaction (reduction or oxidation of chemical substances) occurs at the surface of the metal electrode. The changing potential across the double layer capacitance between the metal electrode and the electrolyte drives the ion flow. For non-faradaic conduction, the metal electrode may be made of metals that are resistant to corrosion and oxidation, for example, titanium or noble metals such as platinum or gold. Despite the lack of chemical interaction between the electrode and the electrolyte, there is transient physical displacement of ions in the electrolyte from the growth and shrinkage of the ion depletion region at the metal-liquid interface, in response to the applied potential. This ion depletion region is referred to as a "double layer" in electrochemistry. Using an electrical engineering model, a parallel plate capacitor forms where the metal is one plate, the depletion region is the dielectric, and the diffuse distribution of ions in the liquid is the other plate. A small signal circuit model for non-faradaic conduction can include the nanopore represented as a simple resistor and the double layer capacitance represented as a capacitor.

Figure 10A:
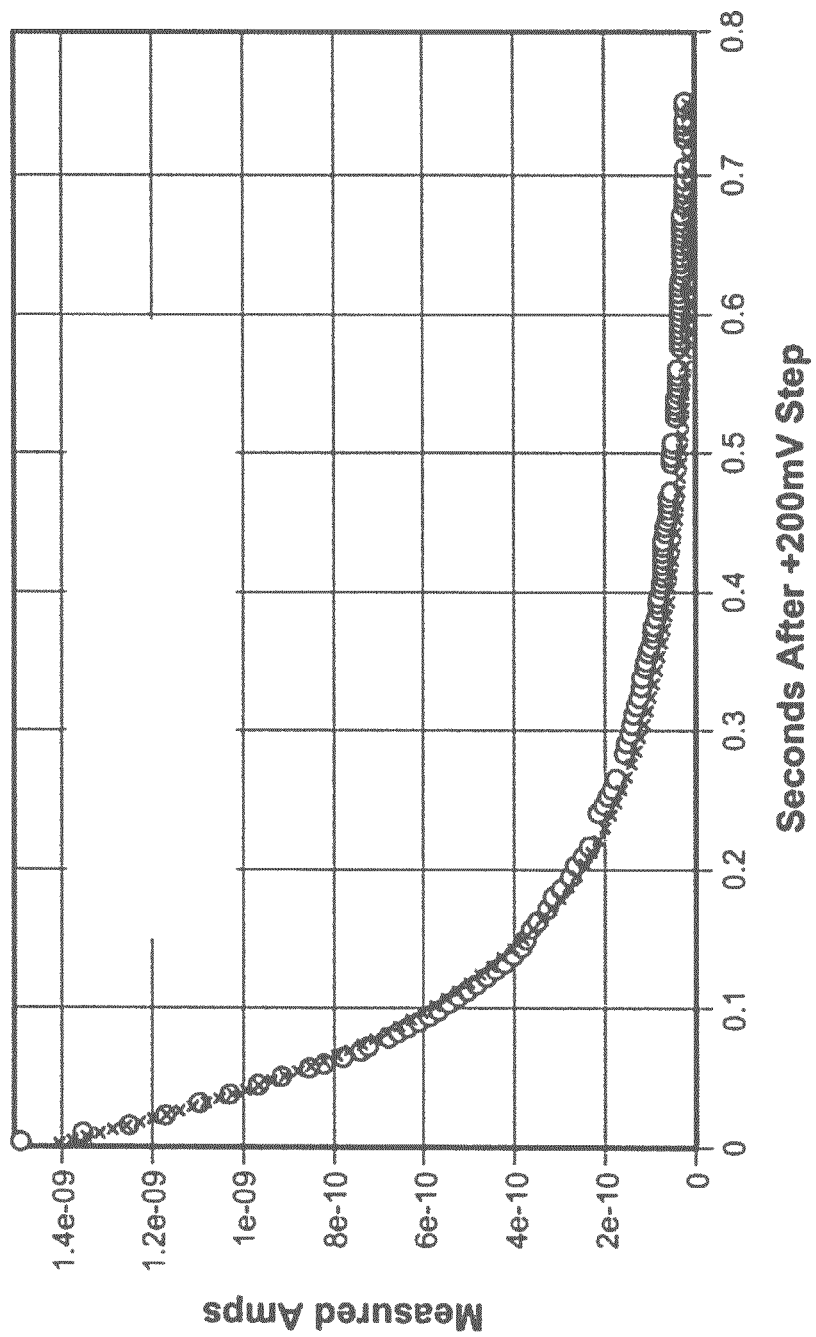
FIG. 10A illustrates decay of measured electrical signals in a non-Faradaic nanopore cell according to embodiments of the present invention.

Unlike the faradaic conduction case, the absolute voltage applied to the electrode is not the same as the voltage applied to the nanopore: the voltage on the double layer biases the potential applied to the nanopore. FIG. 10A illustrates an example of the capacitive response of the double layer according to an embodiment. This figure illustrates the properties of the double layer with a short circuit between the electrolyte and the working electrode. Water viscosity prevents the easy flow of ions in response to the applied field; this is manifested as a series resistance in the double layer capacitive response. This resistance limits the peak current as shown in FIG. 10A. The series nature of the RC electrochemical connection can be seen in the decay of the response, which is characterized by the RC time constant. The electrical properties of the non-Faradaic cell are described in more detail in U.S. Pat. No. 9,551,697, the content of which is incorporated herein by reference in its entirety.

Figure 10B:
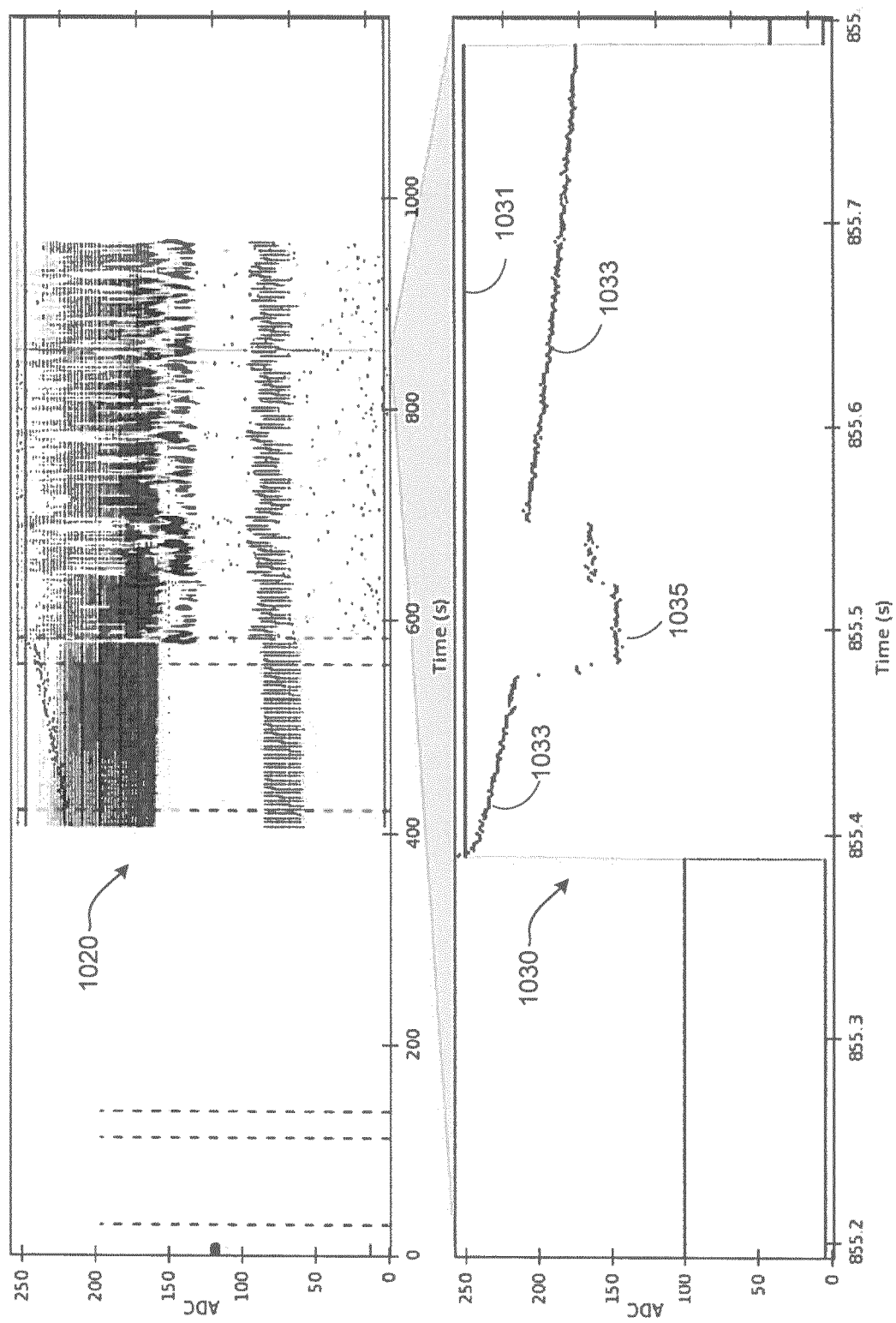
FIG. 10B illustrates another example of decay of measured electrical signals in a non-Faradaic nanopore cell according to embodiments of the present invention.

FIG. 10B illustrates an example of decay of measured electrical signals in a non-Faradaic nanopore cell during a sequencing operation according to embodiments of the present invention. In the upper diagram, 1020 shows raw measured electrical signals of the sequencing operation. In the lower diagram, 1030 shows a time slice of the electrical signals 1020. The lower diagram shows the voltage applied across the electrodes of the sequencing cell 1031, the measured open channel electrical signal 1033, and measured signal when a nucleic sample is present inside the nanopore 1035. It can be seen that the nanopore voltage, as represented by the open channel signal 1033 continues to decrease with time, even with a constant applied voltage 1020.

Figure 11:
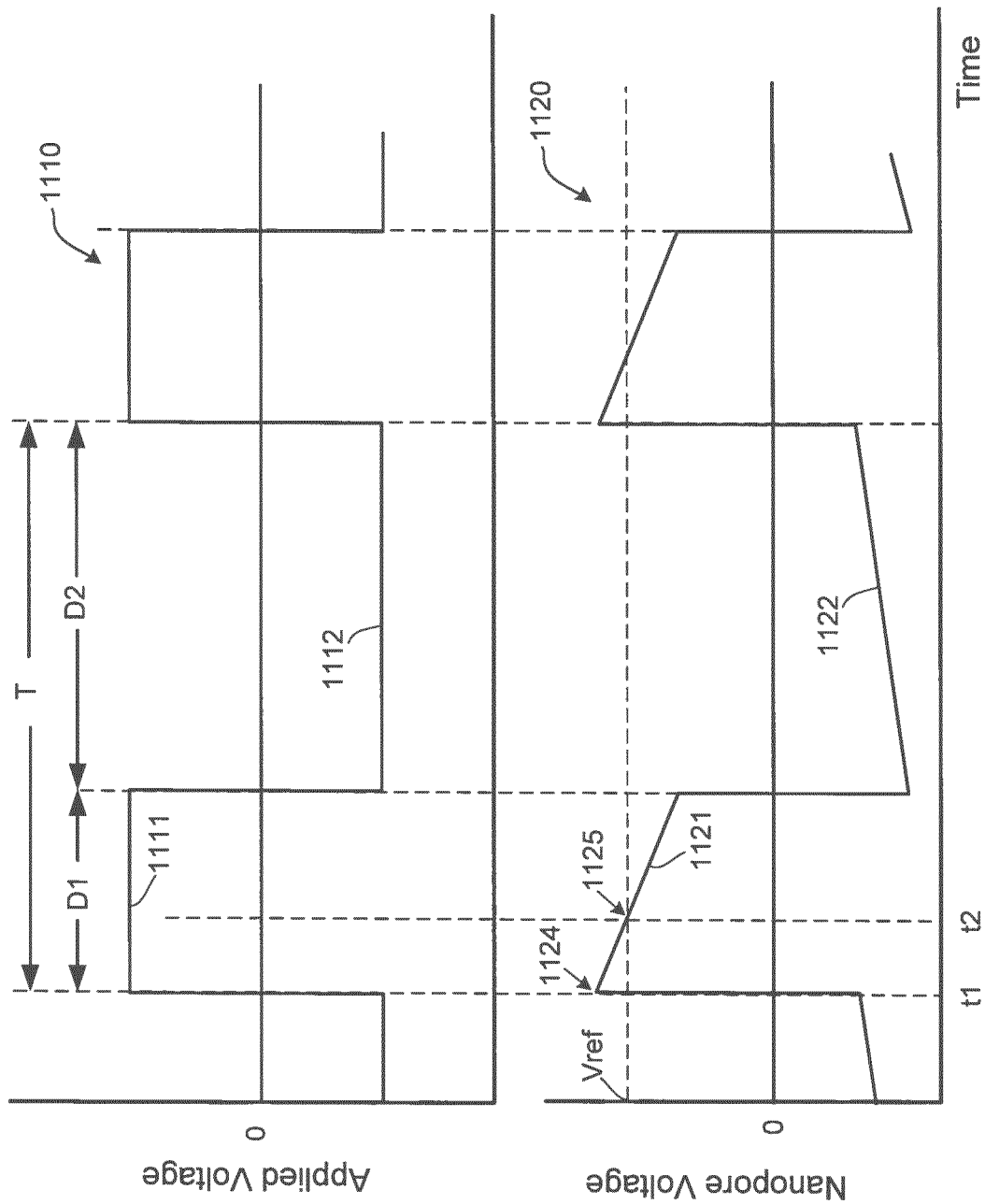
FIG. 11 illustrates decay of nanopore voltage vs. a constant applied voltage in a non-Faradaic nanopore cell according to embodiments of the present invention.

FIG. 11 illustrates applied voltage and nanopore voltage in a non-Faradaic nanopore cell according to some embodiments. In this example, the applied voltage signal 1110 is a periodic signal having a period of T. In each period T, voltage signal 1110 has a first (positive) portion 1111 with a duration D1 and a second (negative) portion 1112 with a duration D2. In duration D1, the magnitude of applied voltage signal 1110 is constant. In duration D2, applied voltage signal 1110 has an opposite polarity, and the magnitude of applied voltage signal 1112 is also constant. The sequencing is carried out in duration D1, when a nucleic acid moves through the nanopore. In duration D2, the applied voltage is reversed. Applying the opposite voltage allows for the ions at the double layer capacitor, which cause the effective voltage across the capacitor to decrease, to flow back through the nanopore so that the cell is initialized to back to a starting state for more sequencing. Such a negative portion of an AC signal can be used in combination with unidirectional speed bumps (as further described herein) so that the nucleic acid does not move backward through the nanopore. In the example of FIG. 11, the duration D1 of the first portion 1111 is about one-third (33%) of the period T, providing a duty cycle of about 33%. In other examples, the duty cycle can be 40% or other suitable values.

In FIG. 11, the nanopore voltage 1120 represents the effective voltage across the nanopore that moves the nucleic acid molecule through the nanopore. In some cases, the nanopore voltage 1120 can be derived from the current through the nanopore. Alternatively, the nanopore voltage 1120 can be directly measured with probes in an experimental arrangement. In each period T, nanopore voltage signal 1120 has a first (positive) portion 1121 with a duration D1 and a second (negative) portion 1122 with a duration D2. In duration D1, the magnitude of nanopore voltage signal 1121 decreases with time, because of the capacitive effect in non-Faradaic conduction. The rate of decrease can be exponential, depending on the capacitive and resistive components of the nanopore cell. For simplicity of illustration, the nanopore voltage 1121 is shown to decrease linearly. Similarly, in duration D2, nanopore voltage signal 1122 has an opposite polarity, and the magnitude of nanopore voltage signal 1122 decreases with time. In both D1 and D2, the rate of decrease depends on the applied voltage 1111 and the capacitance in the non-Faradaic nanopore cell.

In FIG. 11, at time t1, the beginning of duration D1, applied voltage 1111 is applied to the nanopore cell, and the nanopore voltage 1124 is higher than a reference voltage Vref that represents a voltage needed to move the nucleic acid molecule through the nanopore for the sequencing operation. However, the positive portion 1121 of the nanopore voltage decreases with time because of the capacitive effects in the non-Faradaic nanopore cell. At time t2, nanopore voltage 1121 drops to 1125, which is equal to Vref. Beyond time t2, nanopore voltage 1121 drops below Vref, and the nanopore cell is no longer capable of moving the nucleic acid molecule through the nanopore for the sequencing operation. As a result, the nanopore cell is operational only during a limited portion of the applied voltage duration. As an example, the applied voltage has a positive portion of about 2 seconds, and the usable portion can be only about 500 milliseconds (msec). Therefore, a more effective method for the nanopore operation is highly desired.

IV. Increasing Voltage for Non-Faradaic Cell

In some embodiments of the invention, a method is provided for sequencing a nucleic acid molecule, for example, a single strand DNA molecule. The method provides an applied voltage that is sufficient for sequencing a single strand DNA over an extended period of time. For example, a voltage with an increasing magnitude can be applied to the nanopore cell to maintain a nanopore voltage with enough magnitude to perform the sequencing throughout the duration of the applied voltage.

Figure 12:
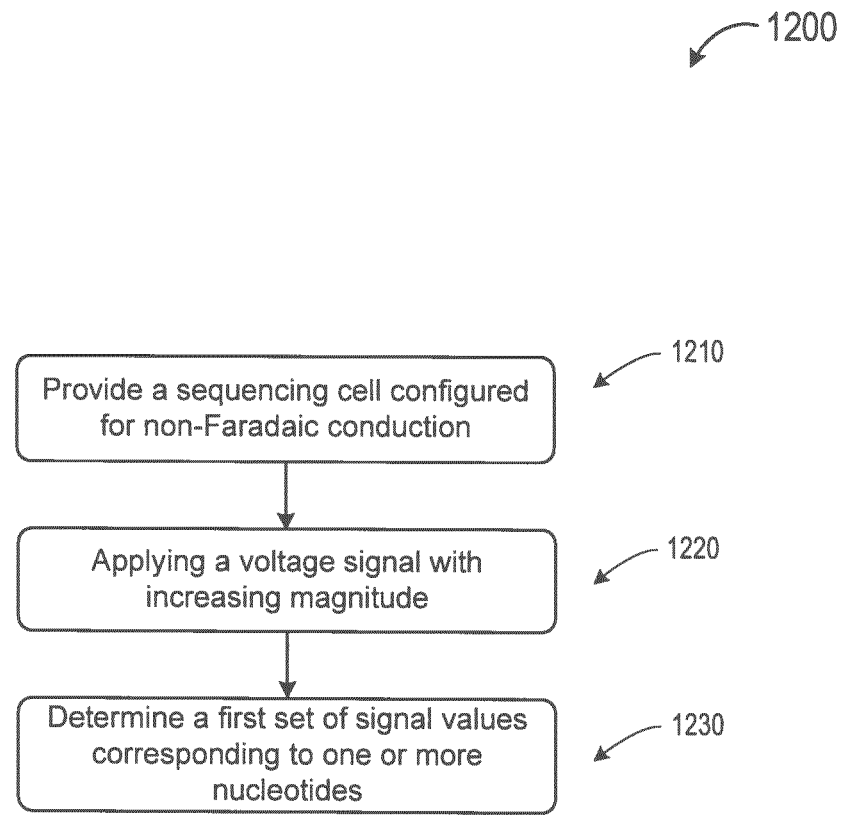
FIG. 12 is a flowchart illustrating a method for sequencing a nucleic acid molecule according to embodiments of the present invention.

FIG. 12 is a flowchart illustrating a method for sequencing a nucleic acid molecule according to some embodiments. The method can be used in combination with cells described above in connection with FIG. 1-6.

At block 1210, method 1200 includes providing a sequencing cell configured for non-Faradaic conduction. The sequencing cell has a nanopore in a membrane that resides over a well. An example of such a sequencing cell is described above in connection with FIG. 6. The sequencing cell includes a first electrode at a bottom of the well, a second electrode in a chamber above the membrane, and an electrolyte in the well and the chamber. The first electrode is configured to facilitate non-Faradaic conduction of ionic current and forms a capacitance with ions in the electrolyte.

At block 1220, the method includes applying a voltage signal with increasing magnitude. A first voltage signal is applied across the first electrode and the second electrode, thereby creating a force that moves the nucleic acid molecule in the sequence cell through the nanopore. As described above, if the voltage across the nanopore falls below a usable voltage value, the sequencing cell stops moving the nucleic acid molecule through the nanopore. In order prevent the voltage across the nanopore from falling below a usable voltage value, the first voltage signal is configured to increase to compensate for a change in the capacitance at the first electrode during application of the first voltage signal.

At block 1230, the method also includes determining a first set of signal values corresponding to one or more nucleotides. The sequencing is carried out by determining a first set of signal values measured during the first voltage signal, the first set of signal values corresponding to one or more nucleotides in the nucleic acid molecule.

Depending on the embodiment, the applied voltage signal can be increased in different forms. For example, the voltage signal can be increased at a predetermined rate. The rate at which the voltage signal increases can be determined from a discharging characteristic of the sequencing cell. The discharging characteristic of the sequencing cell can be described by an RC (Resistance-Capacitance) time constant. Alternatively, the discharging characteristic of the sequencing cell can be described numerically, for example, by a series of voltage signals that changes with time. Based on the discharging characteristic, the rate of change of the voltage signal can be determined. For example, the voltage signal can have a linearly increasing magnitude. In another example, the voltage signal can be an exponentially increasing magnitude. In still another example, the voltage signal can be monitored and modified using a feedback control mechanism. These alternatives are described in more detail in the examples below.

A. Linearly Increasing Applied Voltage

Figure 13A:
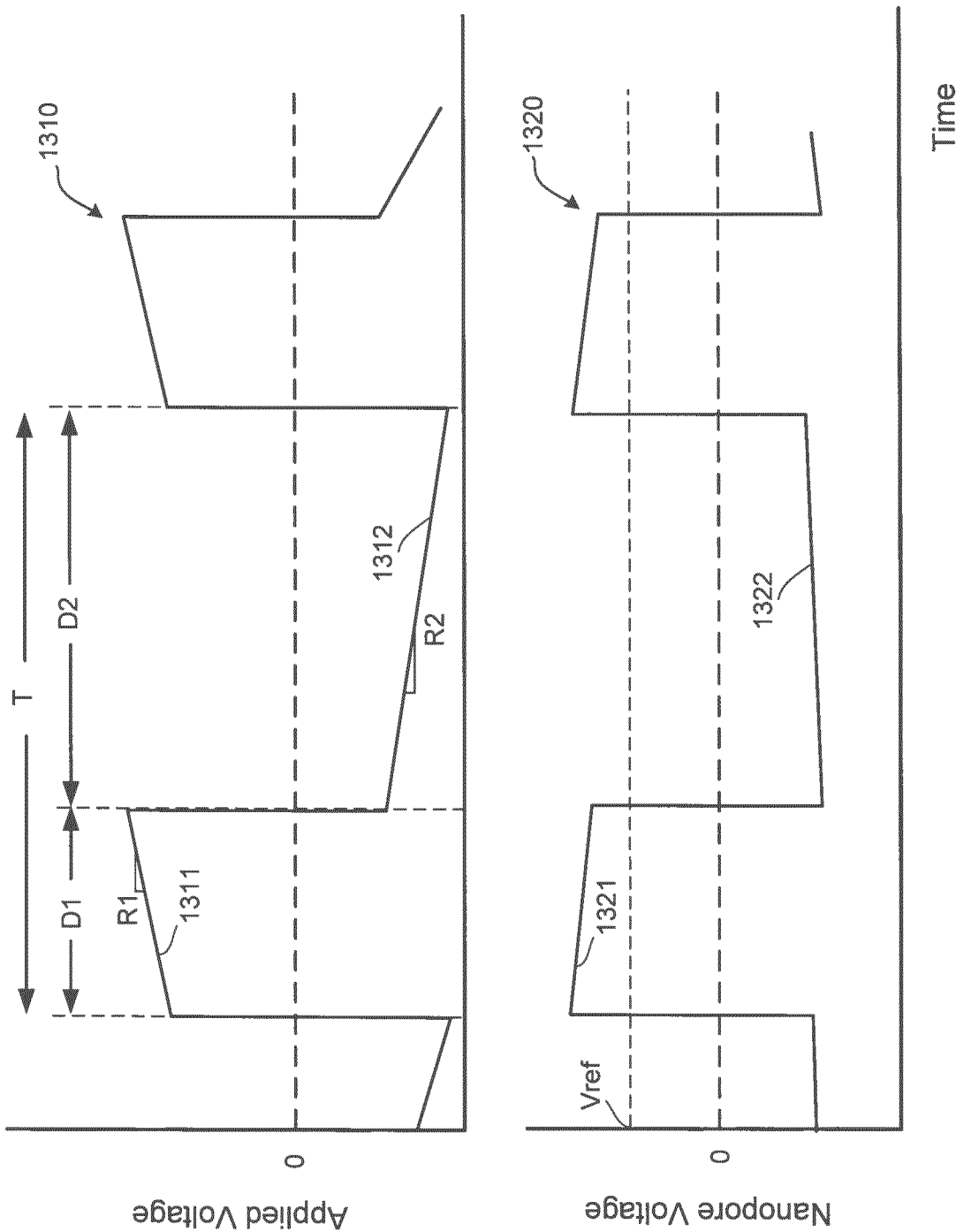
FIG. 13A illustrates nanopore voltage vs. a linearly increasing applied voltage in a non-Faradaic nanopore cell according to embodiments of the present invention.

FIG. 13A illustrates a linearly increasing applied voltage and nanopore voltage in a non-Faradaic nanopore cell according to some embodiments. In this example, the applied voltage signal 1310 is a periodic signal having a period of T. In each period, voltage signal 1310 has a first (positive) portion 1311 with a duration D1 and a second (negative) portion 1312 with a duration D2. In duration D1, the magnitude of applied voltage signal 1310 increases linearly at a rate of R1 mV/sec to compensate the capacitive effect in the non-Faradaic cell. In duration D2, applied voltage signal 1310 has an opposite polarity, and the magnitude of applied voltage signal 1312 increases linearly at a rate of R2 mV/sec. In the example of FIG. 13A, the duration D1 of the first portion 1311 is about one-third (33%) of the period T, providing a duty cycle of about 33%. In other examples, the duty cycle can be 40% or other suitable values.

In FIG. 13A, the nanopore voltage 1320 represents the effective voltage across the nanopore that moves the nucleic acid molecule through the nanopore. In some cases, the nanopore voltage 1320 can be derived from the current through the nanopore. Alternatively, the nanopore voltage 1320 can be directly measured with probes in an experimental arrangement.

In each period T, nanopore voltage signal 1320 has a first (positive) portion 1321 with a duration D1 and a second (negative) portion 1322 with a duration D2. In duration D1, the magnitude of nanopore voltage signal 1321 decreases with time, if the applied voltage 1310 is not sufficient to overcome the capacitive effect. Similarly, in duration D2, nanopore voltage signal 1322 has an opposite polarity, and the magnitude of nanopore voltage signal 1322 decreases with time. In both D1 and D2, the rate of decrease depends on the applied voltage 1311 and the capacitance in the non-Faradaic nanopore cell. It is noted that in duration D1, the magnitude of nanopore voltage signal 1321 is higher than the voltage Vref needed to move the nucleic acid molecule through the nanopore. Therefore, throughout the period D1, the nanopore can continuously move the nucleic acid molecule through the nanopore for sequencing.

In the applied voltage 1310, the rate of increase R1 of the positive portion 1311 can be determined experimentally to ensure that the nanopore voltage is maintained above the voltage Vref needed to move the nucleic acid molecule through the nanopore. In some examples, the duration D1 of the positive portion 1311 of the applied voltage can be between 0.5 to 2.0 seconds. In other examples, the duration D1 of the positive portion 1311 of the applied voltage can be between 2.0 to 5.0 seconds. In still other examples, the duration D1 of the positive portion 1311 of the applied voltage can be between 5.0 to 20.0 seconds. In other examples, the duration D1 of the positive portion 1311 of the applied voltage can be longer than 20.0 seconds, for example, 30 seconds, 50 seconds, or longer.

B. Stepwise Increasing Applied Voltage

Figure 13B:
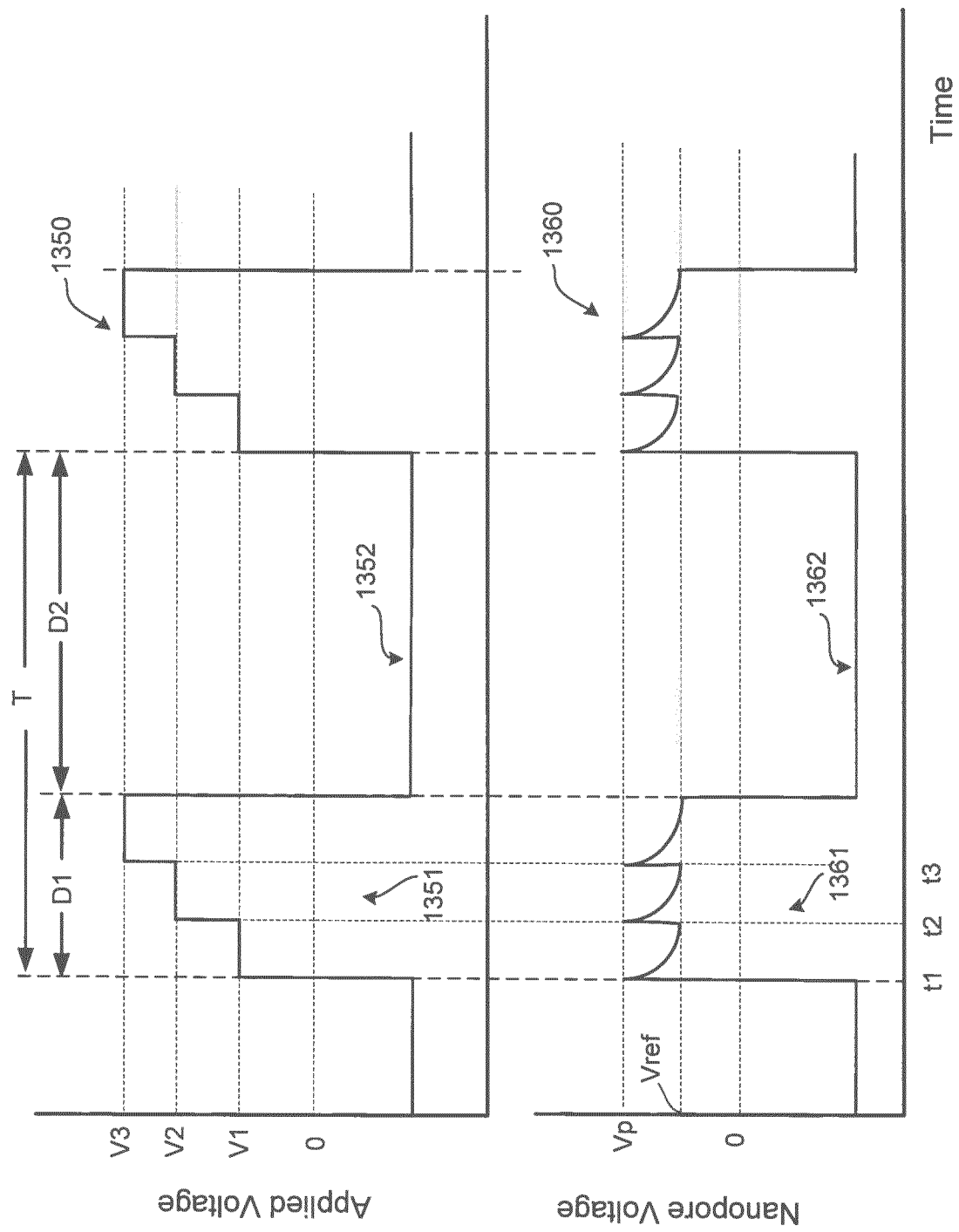
FIG. 13B illustrates nanopore voltage vs. a stepwise applied voltage in a non-Faradaic nanopore cell according to embodiments of the present invention.

FIG. 13B illustrates a stepwise applied voltage and nanopore voltage in a non-Faradaic nanopore cell according to some embodiments. In order to maintain a usable nanopore voltage, the magnitude of the applied voltage is increased in steps, such that the nanopore voltage is maintained at or above a preset reference voltage that represents the usable nanopore voltage for the sequencing operation. The height of the voltage steps and the timing of the voltage changes can be determined experimentally or with the aid of simulation, or a combination of these methods.

In the example of FIG. 13B, the applied voltage signal 1350 is a periodic signal having a period of T. In each period, voltage signal 1350 has a first (positive) portion 1351 with a duration D1 and a second (negative) portion 1352 with a duration D2. In duration D1, the magnitude of applied voltage signal 1350 is configured to increase in a stepwise manner. In each period T, nanopore voltage signal 1360 has a first (positive) portion 1361 with a duration D1 and a second (negative) portion 1362 with a duration D2. The nanopore voltage 1360 represents the effective voltage across the nanopore that moves the nucleic acid molecule through the nanopore. In some cases, the nanopore voltage 1360 can be derived from the current through the nanopore. Alternatively, the nanopore voltage 1360 can be directly measured with probes in an experimental arrangement.

In duration D2, applied voltage signal 1350 has an opposite polarity, and the magnitude of applied voltage signal 1352 is shown to be constant in FIG. 13B, but can increase with time as needed. In the example of FIG. 13B, the duration D1 of the first portion 1351 is about one-third (33%) of the period T, providing a duty cycle of about 33%. In other examples, the duty cycle can be 40% or other suitable values.

In FIG. 13B, at time t1, an applied voltage having a magnitude V1 is applied to the sequencing cell, resulting in a nanopore voltage of Vp, which is greater than Vref, the nanopore voltage usable for sequencing. Due to the capacitive nature of the non-Faradaic cell, the nanopore voltage drops with time. At time t2, the nanopore voltage drops to Vref. At this time, the system increases the applied voltage to V2, bringing the nanopore voltage back up to Vp. The sequencing operation continues until t3, when the nanopore voltage again drops to Vref. This condition causes the system to increase the applied voltage to V3. The magnitude of voltage steps for V1, V2, and V3, etc., and the timing of the voltage changes for t1, t2, and t3, etc., can be determined experimentally or with the aid of simulation, or a combination of these methods. The stepwise increase of applied voltage continues throughout duration D1 to maintain the nanopore voltage at or above Vref. Therefore, throughout the period D1, the nanopore can continuously move the nucleic acid molecule through the nanopore for sequencing.

In duration D2, nanopore voltage signal 1362 has an opposite polarity, and the magnitude of nanopore voltage signal decreases with time, if the applied voltage is constant. To simplify the drawings, both applied voltage 1352 and nanopore voltage signal 1362 in duration D2 are shown as constant. In some embodiments, the stepwise applied voltage can also be applied in duration D2.

In some examples, the duration D1 of the positive portion 1351 of the applied voltage can be 0.5 to 2.0 seconds. In other examples, the duration D1 of the positive portion 1351 of the applied voltage can be 2.0 to 5.0 seconds. In still other examples, the duration D1 of the positive portion 1351 of the applied voltage can be 5.0 to 20.0 seconds. In other examples, the duration D1 of the positive portion 1351 of the applied voltage can be longer than 20.0 seconds, for example, 30 seconds, 50 seconds, or longer.

C. Exponentially Increasing Applied Voltage

Figure 14:
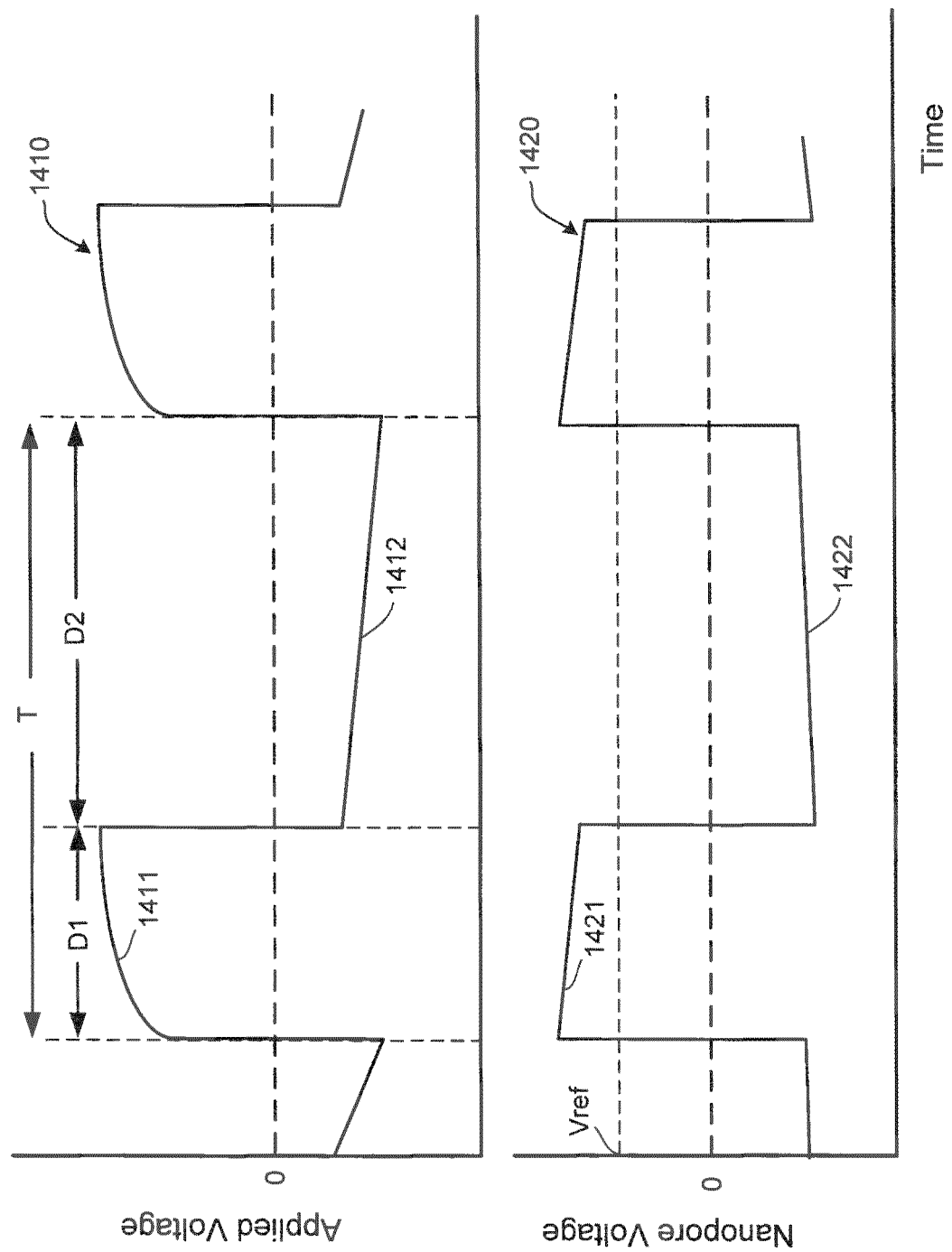
FIG. 14 illustrates nanopore voltage vs. an exponentially increasing applied voltage in a non-Faradaic nanopore cell according to embodiments of the present invention.

FIG. 14 illustrates an exponentially increasing applied voltage and nanopore voltage in a non-Faradaic nanopore cell according to some embodiments. In this example, the applied voltage signal 1410 is a periodic signal having a period of T. In each period, voltage signal 1410 has a first (positive) portion 1411 with a duration D1 and a second (negative) portion 1412 with a duration D2. In duration D1, the magnitude of applied voltage signal 1410 increases exponentially. In duration D2, applied voltage signal 1410 has an opposite polarity, and the magnitude of applied voltage signal 1412 increases linearly or exponentially. In the example of FIG. 14, the duration D1 of the first portion 1411 is about one-third (33%) of the period T, providing a duty cycle of about 33%. In other examples, the duty cycle can be 40% or other suitable values.

In FIG. 14, the nanopore voltage 1420 represents the effective voltage across the nanopore that moves the nucleic acid molecule through the nanopore. In some cases, the nanopore voltage 1420 can be derived from the current through the nanopore. Alternatively, the nanopore voltage 1420 can be directly measured with probes in an experimental arrangement.

In each period T, nanopore voltage signal 1420 has a first (positive) portion 1421 with a duration D1 and a second (negative) portion 1422 with a duration D2. In duration D1, the magnitude of nanopore voltage signal 1421 decreases with time, if the applied voltage 1410 is not sufficient to overcome the capacitive effect. Similarly, in duration D2, nanopore voltage signal 1422 has an opposite polarity, and the magnitude of nanopore voltage signal 1422 decreases time. In both D1 and D2, the rate of decrease depends on the applied voltage 1411 and the capacitance in the non-Faradaic nanopore cell. It is noted that in duration D1, the magnitude of nanopore voltage signal 1421 is higher than the voltage Vref needed to move the nucleic acid molecule through the nanopore. Therefore, throughout the period D1, the nanopore can continuously move the nucleic acid molecule through the nanopore for sequencing.

In the applied voltage 1410, the rate of increase of the positive portion 1411 can be determined experimentally to ensure that the nanopore voltage is maintained above the voltage Vref needed to move the nucleic acid molecule through the nanopore. In some examples, the duration D1 of the positive portion 1411 of the applied voltage can be 0.5 to 2.0 seconds. In other examples, the duration D1 of the positive portion 1411 of the applied voltage can be 2.0 to 5.0 seconds. In still other examples, the duration D1 of the positive portion 1411 of the applied voltage can be 5.0 to 20.0 seconds. In other examples, the duration D1 of the positive portion 1411 of the applied voltage can be longer than 20.0 seconds, for example, 30 seconds, 50 seconds, or longer.

V. Applied Voltage with Agitation Pulses

For embodiments that use speed bumps, it can be advantageous to use agitation pulses to cause the speed bumps to be removed or pass through the nanopore more quickly. Having the speed bumps can help to prevent the nucleic acid from moving too fast to obtain an accurate, but they can cause the sequencing throughput to decrease too much. The agitation pulses can help to balance the tradeoff and control the speed of the nucleic acid through the nanopore.

A. Applied Signal

Figure 15:
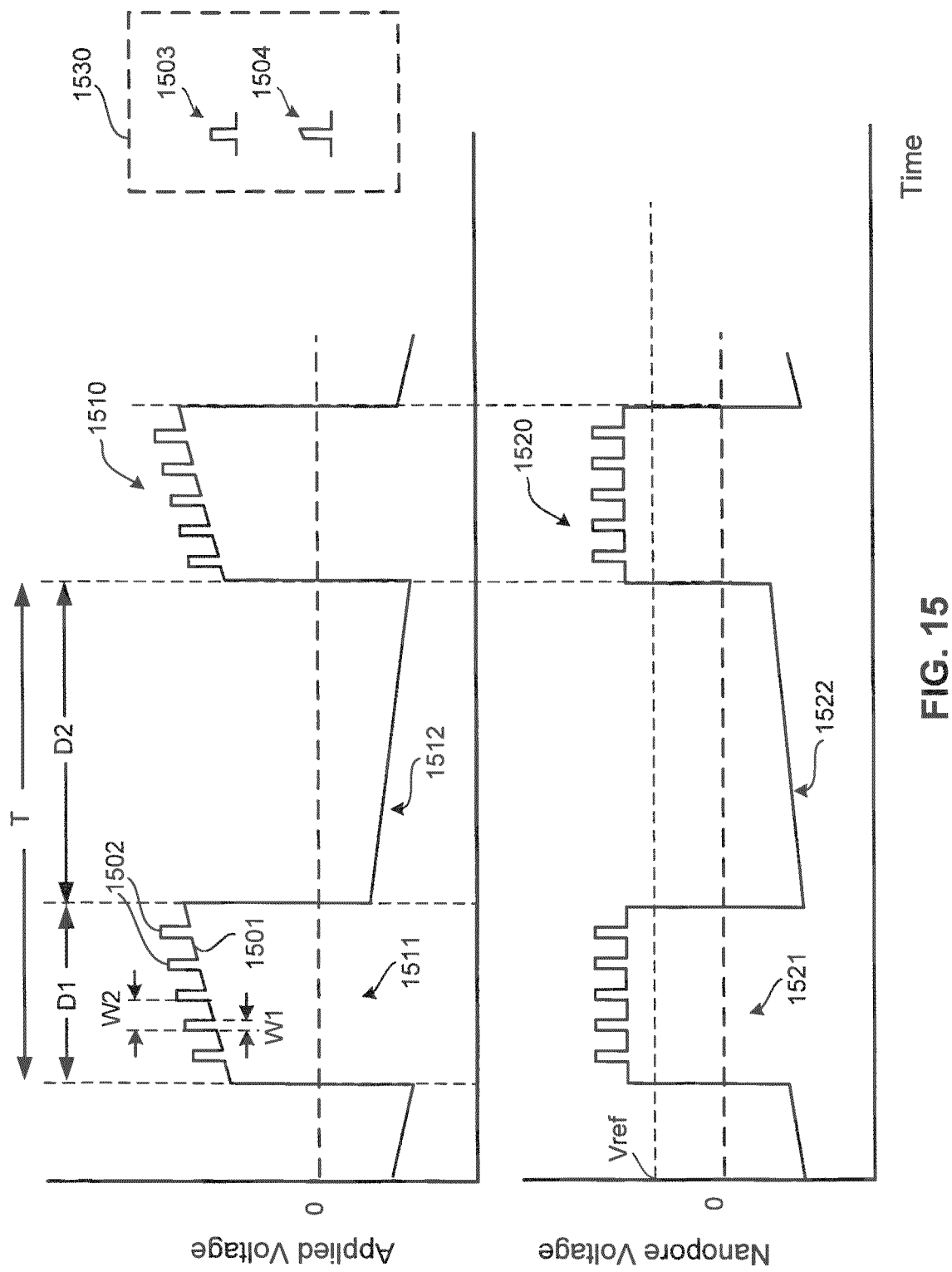
FIG. 15 illustrates nanopore voltage vs. an increasing applied voltage including agitation pulses in a non-Faradaic nanopore cell according to embodiments of the present invention.

FIG. 15 illustrates an increasing applied voltage including agitation pulses and nanopore voltage in a non-Faradaic nanopore cell according to some embodiments. In these embodiments, the applied voltage signals can have a number of narrow voltage pulses superimposed over a base voltage.

In FIG. 15, the applied voltage signal 1510 is a periodic signal having a period of T. In each period, voltage signal 1510 has a first (positive) portion 1511 with a duration D1 and a second (negative) portion 1512 with a duration D2. In duration D1, the applied voltage 1511 includes a base voltage 1501 and multiple agitation voltage pulses 1502. In this example, the magnitude of base voltage signal 1501 is shown to increase linearly, but it can also increase in different ways, for example, increasing exponentially. In some cases, the base voltage can be a constant. The agitation pulses 1502 can have a width of W1 and a period of W2. In duration D2, the applied voltage signal has an opposite polarity, and the magnitude of applied voltage signal 1512 can increase with time in different fashions, for example, linearly or exponentially. In duration D2, the applied voltage 1512 may or may not have agitation pulses. In the example of FIG. 15, the duration D1 of the first portion 1511 is about one-third (33%) of the period T, providing a duty cycle of about 33%. In other examples, the duty cycle can be 40%, 50%, or other suitable values.

In FIG. 15, the nanopore voltage 1520 represents the effective voltage across the nanopore that moves the nucleic acid molecule through the nanopore. In some cases, the nanopore voltage 1520 can be derived from the current through the nanopore, for example, using circuit analysis or simulation techniques. Alternatively, the nanopore voltage 1520 can be directly measured with probes in an experimental arrangement. As shown in FIG. 15, the positive portion 1521 of the nanopore voltage 1520 stays above a reference voltage Vref that represents a voltage needed to move the nucleic acid molecule through the nanopore.

In each period T, nanopore voltage signal 1520 has a first (positive) portion 1521 with a duration D1 and a second (negative) portion 1522 with a duration D2. In duration D1, the magnitude of nanopore voltage signal 1521 is shown to have a flat base voltage. However, the base voltage may decrease with time, if the applied voltage 1510 is not sufficient to overcome the capacitive effect. Nanopore voltage signal 1521 in duration D1 can also have multiple agitation pulses in response to the applied voltage. In duration D2, nanopore voltage signal 1522 has an opposite polarity, and the magnitude of nanopore voltage signal 1522 decreases with time. In both D1 and D2, the rate of change of the nanopore voltage depends on the applied voltage 1511 and the capacitance in the non-Faradaic nanopore cell. It is noted that in duration D1, the magnitude of nanopore voltage signal 1521 is higher than the voltage Vref needed to move the nucleic acid molecule through the nanopore. Therefore, throughout the period D1, the nanopore can continuously move the nucleic acid molecule through the nanopore for sequencing.

In the applied voltage 1510, the rate of increase R1 of the positive portion 1511 can be determined experimentally to ensure that the nanopore voltage is maintained above the voltage Vref needed to move the nucleic acid molecule through the nanopore. In some examples, the duration D1 of the positive portion 1511 of the applied voltage can be 0.5 to 2.0 seconds. In other examples, the duration D1 of the positive portion 1511 of the applied voltage can be 2.0 to 5.0 seconds. In still other examples, the duration D1 of the positive portion 1511 of the applied voltage can be 5.0 to 20.0 seconds. In other examples, the duration D1 of the positive portion 1511 of the applied voltage can be longer than 20.0 seconds, for example, 30 seconds, 50 seconds, or longer.

As an example, as a strand of nucleic acid molecule is pulled through the nanopore, a stopper or speed bump holds the strand at the nanopore for a period of time, and the double strand portion is dehybridized and floats off. During this time, a sequencing reading can be performed. In embodiments of the invention, the agitation pulses can speed up the movement of the nucleic acid molecule in the sequence cell through the nanopore. In some embodiments, the width of the agitation pulse W1 can be about 0.1 milliseconds, and the period of the agitation pulses W2 can be about 2.0 milliseconds. In some embodiments, the magnitude of the base voltage can be about 120 millivolts, and the height of the agitation pulses can be about 80 millivolts. In some examples, the applied voltage can have one and a half seconds to two seconds positive portion D1 and two or three seconds negative portion D2, for a 40% duty cycle. In this case, the period T of the applied voltage can be about 5 sec, with D1=2 seconds and D2=3 seconds. These parameters can be adjusted for specific applications.

In some embodiments, using the method of FIG. 15, the sequencing cell can be configured to move a DNA base through the nanopore every 100 milliseconds. In this arrangement, 20 bases can be sequenced every two seconds. In some embodiments, 150 bases or 200 bases of DNA can be sequenced in a minute, which can enable many useful applications.

In FIG. 15, the agitation pulses 1502 are shown to have a constant magnitude. However, the agitation voltage pulses can have different shapes. As shown in the inset 1530 in FIG. 15, agitation voltage pulse 1503 has a constant magnitude, and agitation pulse 1504 has a sloped shape. In some examples, the shape of the agitation pulse can reflect the shape of the base portion of the applied voltage signal. In other examples, the shape of the agitation pulse can be independently configured.

B. Electric Circuit for Agitation Pulses in Nanopore Sequencing Cell

Figure 16:
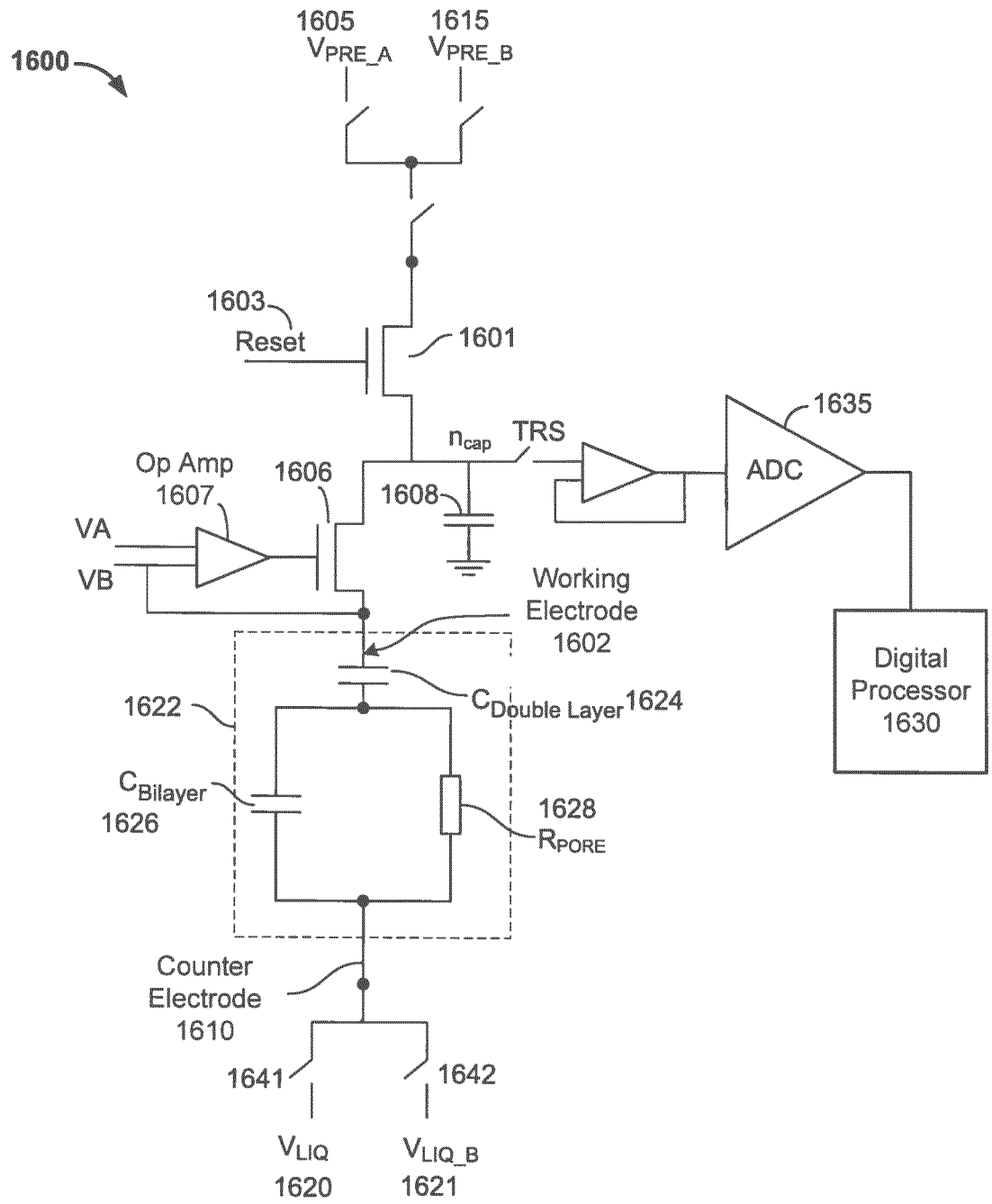
FIG. 16 illustrates an electric circuit for a nanopore cell according to embodiments of the present invention.

FIG. 16 illustrates an embodiment of an electric circuit 1600 (which may include portions of electric circuit 222 in FIG. 2) in a nanopore cell, such as nanopore cells 200 in FIGS. 2 and 600 in FIG. 6. In some embodiments, electric circuit 1600 is similar to electric circuit 400 in FIG. 4, and detailed description of the similar components are not repeated here. For example, electric circuit 1600 includes a counter electrode 1610 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 608 in FIG. 6) in contact with the lipid bilayer (e.g., lipid bilayer 614) in the nanopore cells by connecting to a voltage source $V_{LIQ}$ 1620 or a voltage source $V_{LIQ\_B}$ 1621. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. Voltage sources $V_{LIQ}$ 1620 and $V_{LIQ\_B}$ 1621, along with switches 1641 and 1642, can be used to apply the agitation pulses superimposed on the base voltage as described above in connection with FIG. 15.

FIG. 16 also shows an electrical model 1622 representing the electrical properties of a working electrode 1602 and the lipid bilayer. Electrical model 1622 includes a capacitor 1626 ($C_{Bilayer}$) that models a capacitance associated with the lipid bilayer and a resistor 1628 ($R_{PORE}$) that models a variable resistance associated with the nanopore, which can change based on the presence of a particular tag in the nanopore. Electrical model 1622 also includes a capacitor 1624 having a double layer capacitance ($C_{Double\ Layer}$) and representing the electrical properties of the working electrode and well. The working electrode may be configured to apply a distinct potential independent from the working electrodes in other nanopore cells.

An operational amplifier 1607 and a transistor 1606 form a voltage regulator. Operational amplifier 1607 has two inputs VA and VB. The voltage regulator maintains the working electrode voltage at VA to provide a voltage stimulus to be applied across the nanopore in the nanopore cell. Such an optional part of the circuit can be used when measuring changes in current required to maintain a constant voltage.

Circuitry 1600 may further include an on-chip integrating capacitor 1608 ($n_{cap}$). Integrating capacitor 1608 may be pre-charged by using a reset signal 1603 to close switch 1601, such that integrating capacitor 1608 is connected to voltage sources $V_{PRE\_A}$ 1605 or $V_{PRE\_B}$ 1615. In some embodiments, the voltage source provide a constant reference voltage. When switch 1601 is closed, integrating capacitor 1608 may be pre-charged to the reference voltage level of voltage sources $V_{PRE\_A}$ 1605 or $V_{PRE\_B}$ 1615.

A digital processor 1630 can process the ADC output data, e.g., for normalization, data buffering, data filtering, data compression, data reduction, event extraction, or assembling ADC output data from the array of nanopore cells into various data frames. In some embodiments, digital processor 1630 can perform further downstream processing, such as base determination. Digital processor 1630 can be implemented as hardware (e.g., in a GPU, FPGA, ASIC, etc.) or as a combination of hardware and software.

C. Benefit of Using Agitation Pulses

Figure 17:
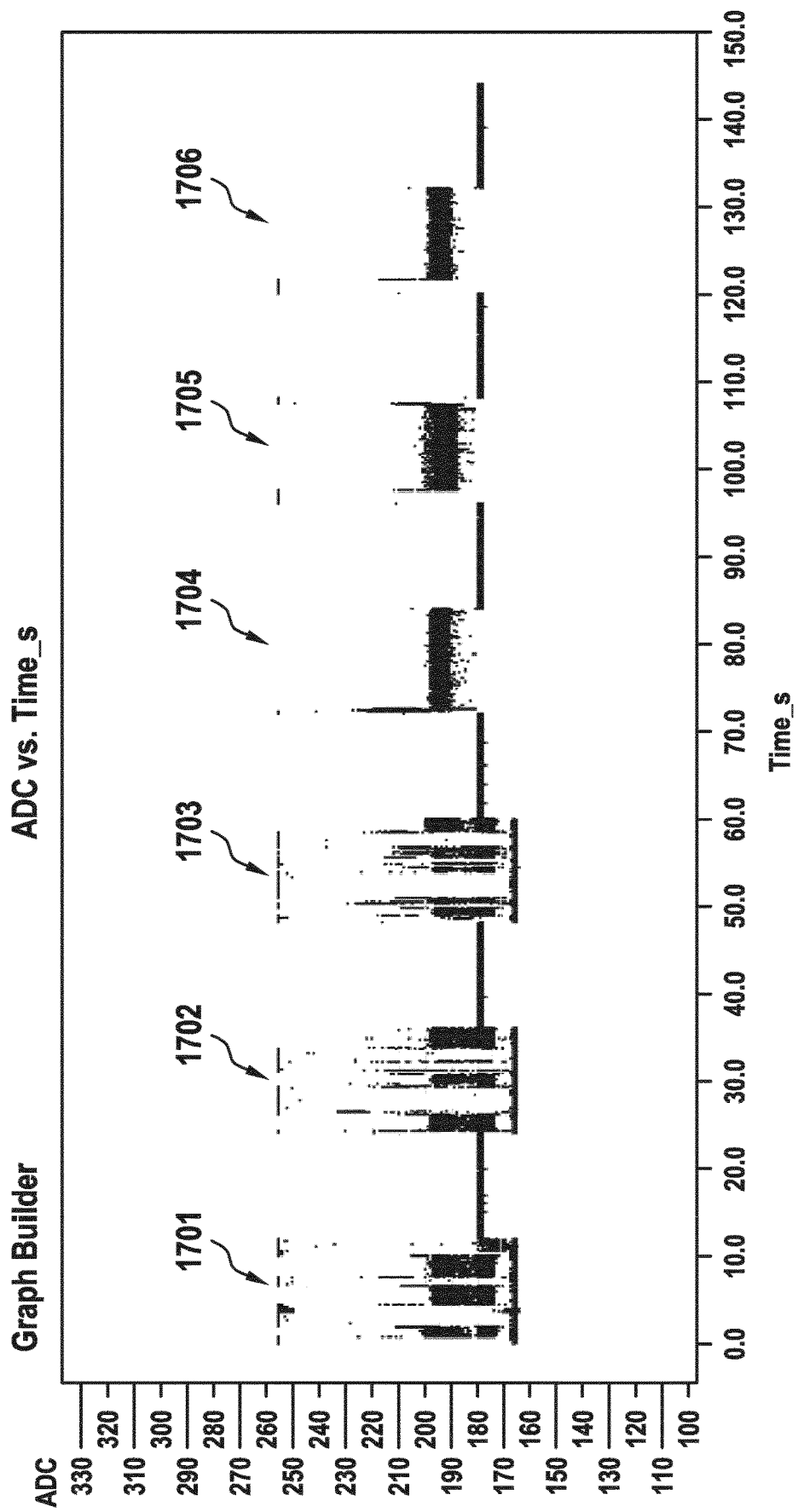
FIG. 17 shows an example data points captured from a nanopore cell that illustrates the effectiveness of the applied voltage with agitation pulses according to some embodiments of the invention.

FIG. 17 shows an example of data points captured from a nanopore cell that can illustrate the effectiveness of the applied voltage with agitation pulses according to some embodiments of the invention. FIG. 17 illustrates output data points from a nanopore cell with six cycles of applied voltage 1701 to 1706. In each of the first to third cycles 1701, 1702, and 1703, a pulsed DC waveform was applied, each with a base voltage and multiple agitation pulses superimposed on the base voltage. In each of the fourth to sixth cycles 1704, 1705, and 1706, a flat DC waveform was applied.

The output data points in the first to third cycle 1701, 1702, and 1703 shows that three or more speed bumps have passed through or removed so that sequencing measurement could be obtained for three portions of the nucleic acid. On the other hand, the output data points in the fourth to sixth cycle 1704, 1705, and 1706 show only a same portion of the nucleic acid being sequenced the entire cycle.

VI. Dynamically Applied Voltage with Feedback

In some embodiments, a method for sequencing a nucleic acid molecule can include a dynamically applied voltage. In this method, the applied voltage is adjusted as needed to maintain a usable nanopore voltage to continue the sequencing operation.

Figure 18:
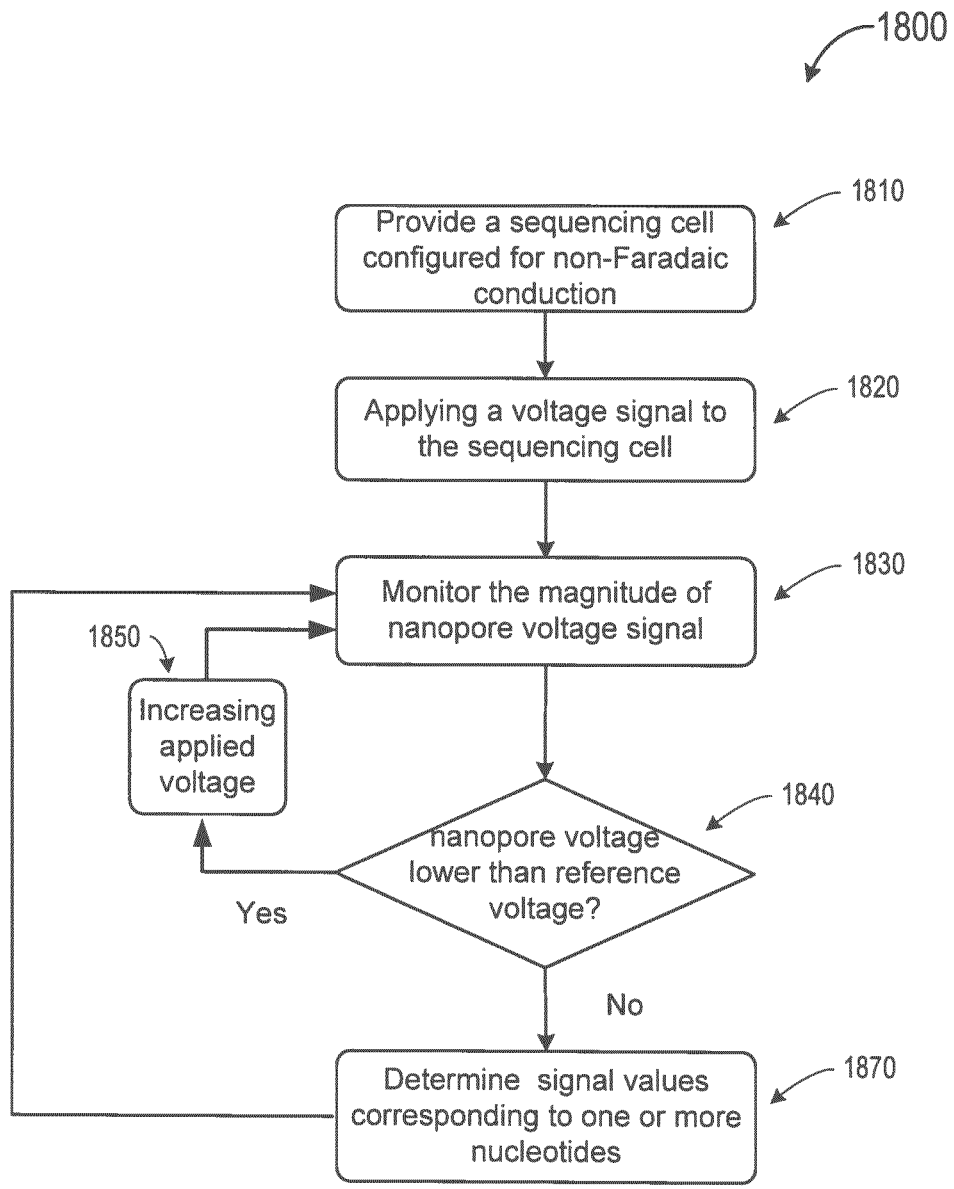
FIG. 18 is a flowchart illustrating a method for sequencing a nucleic acid molecule according to embodiments of the present invention.

FIG. 18 is a flowchart illustrating a method for sequencing a nucleic acid molecule according to some embodiments. The method can be used in combination with cells described above in connection with FIG. 1-6. At block 1810, method 1800 includes providing a sequencing cell configured for non-Faradaic conduction. The method includes providing a sequencing cell with a nanopore in a membrane that resides over a well. An example of such a sequencing cell is described above in connection with FIG. 6. The sequencing cell also includes a first electrode at the bottom of the well, a second electrode in a chamber above the membrane, and an electrolyte in the well and the chamber. The first electrode is configured to facilitate non-Faradaic conduction of ionic current and forms a capacitance with ions in the electrolyte.

At block 1820, the method includes applying a voltage signal to the sequencing cell. The voltage signal is applied across the first electrode and the second electrode, thereby creating a force that moves the nucleic acid molecule in the sequence cell through the nanopore. As described above, if the voltage across the nanopore falls below a usable voltage value, the sequencing cell stops moving the nucleic acid molecule through the nanopore.

At block 1830, in order prevent the voltage across the nanopore from falling below a usable voltage value, the method includes monitoring the magnitude of nanopore voltage signal. Here, the nanopore voltage can be derived from the current through the nanopore, for example, using circuit analysis or simulation techniques. Alternatively, the nanopore voltage can be directly measured with probes in an experimental arrangement.

At block 1840, the method also includes determining if the nanopore voltage is lower than a preset reference voltage. The reference voltage represents a usable nanopore voltage for sequencing operation. As described above, during sequencing, an electrical force is applied to the nanopore to pull a nucleic acid molecule through the nanopore. Due to the capacitive effect, the nanopore voltage can decrease with time and can fall below the voltage needed for the sequencing operation. The preset reference voltage can be determined experimentally or through circuit analysis or simulation techniques. The nanopore voltage can be compared with the reference voltage, and a decision made.

At block 1850, if the magnitude of the nanopore voltage falls below the preset reference voltage, the applied voltage is increased such that the nanopore voltage is higher than the preset reference voltage.

At block 1860, if the nanopore voltage is not lower than the reference voltage, the method proceeds to perform sequencing. The sequencing can be carried out by determining a first set of signal values measured during the first voltage signal, the first set of signal values corresponding to one or more nucleotides in the nucleic acid molecule.

The method can continue to perform sequencing of the nucleic acid molecule with the dynamically adjusted applied voltage. The nanopore voltage can be maintained above the reference voltage Vref that represents a voltage needed to move the nucleic acid molecule through the nanopore.

In alternative embodiments, method 1800 can be implemented by applying a current signal to the sequencing cell at block 1820, instead of applying a voltage signal. The applied current signal can be adjusted based on the nanopore current or voltage determined at block 1840.

Figure 19:
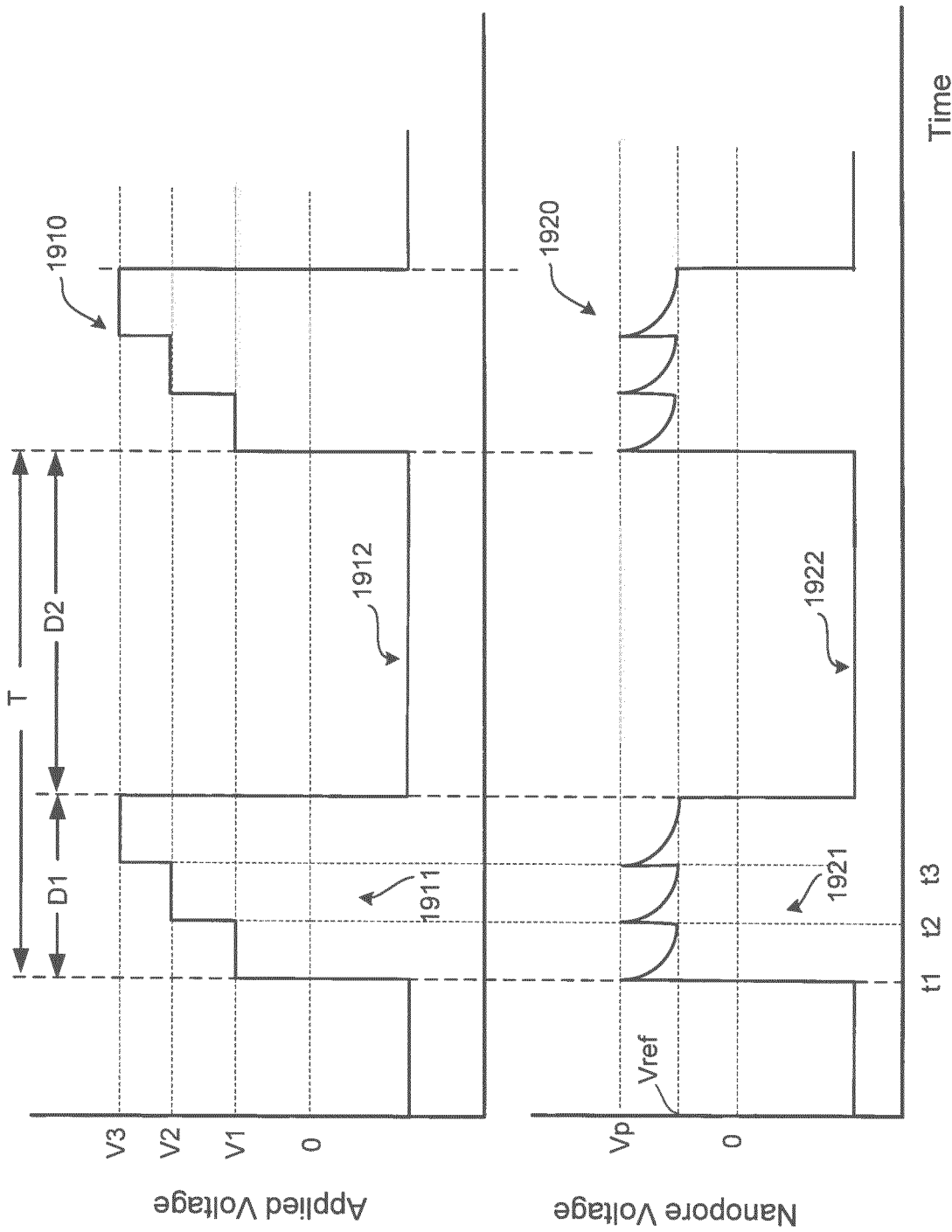
FIG. 19 illustrates nanopore voltage vs. dynamically applied voltage in a non-Faradaic nanopore cell with feedback control according to embodiments of the present invention.

FIG. 19 illustrates applied voltage and nanopore voltage in a non-Faradaic nanopore cell with feedback control according to some embodiments. In order to maintain a usable nanopore voltage, the magnitude of the nanopore voltage is monitored relative to a preset reference voltage that represents the usable nanopore voltage for the sequencing operation. If the magnitude of the nanopore voltage falls below the preset reference voltage, the applied voltage is increased such that the nanopore voltage is higher than the preset reference voltage.

In this example, the applied voltage signal 1910 is a periodic signal having a period of T. In each period, voltage signal 1910 has a first (positive) portion 1911 with a duration D1 and a second (negative) portion 1912 with a duration D2. In duration D1, the magnitude of applied voltage signal 1910 increases in response to changes in the nanopore voltage. In each period T, nanopore voltage signal 1920 has a first (positive) portion 1921 with a duration D1 and a second (negative) portion 1922 with a duration D2. The nanopore voltage 1920 represents the effective voltage across the nanopore that moves the nucleic acid molecule through the nanopore. In some cases, the nanopore voltage 1920 can be derived from the current through the nanopore. Alternatively, the nanopore voltage 1920 can be directly measured with probes in an experimental arrangement.

In duration D2, applied voltage signal 1910 has an opposite polarity, and the magnitude of applied voltage signal 1912 is shown to be constant in FIG. 19, but can increase with time as needed. In the example of FIG. 19, the duration D1 of the first portion 1911 is about one-third (33%) of the period T, providing a duty cycle of about 33%. In other examples, the duty cycle can be 40% or other suitable values.

In FIG. 19, at time t1, an applied voltage having a magnitude V1 is applied to the sequencing cell, resulting in a nanopore voltage of Vp, which is greater than Vref, the nanopore voltage usable for sequencing. Due to the capacitive nature of the non-Faradaic cell, the nanopore voltage drops with time. At time t2, the nanopore voltage drops to Vref. At this time, the system increases the applied voltage to V2, bringing the nanopore voltage back up to Vp. The sequencing operation continues until t3, when the nanopore voltage again drops to Vref. This condition causes the system to increase the applied voltage to V3. This feedback control cycle continues throughout duration D1 to maintain the nanopore voltage at or above Vref. Therefore, throughout the period D1, the nanopore can continuously move the nucleic acid molecule through the nanopore for sequencing.

In duration D2, nanopore voltage signal 1922 has an opposite polarity, and the magnitude of nanopore voltage signal decreases with time, if the applied voltage is constant. To simplify the drawings, both applied voltage 1912 and nanopore voltage signal 1922 in duration D2 are shown as constant. In some embodiments, the feedback method can also be applied in duration D2.

In some examples, the duration D1 of the positive portion 1911 of the applied voltage can be 0.5 to 2.0 seconds. In other examples, the duration D1 of the positive portion 1911 of the applied voltage can be 2.0 to 5.0 seconds. In still other examples, the duration D1 of the positive portion 1911 of the applied voltage can be 5.0 to 20.0 seconds. In other examples, the duration D1 of the positive portion 1911 of the applied voltage can be longer than 20.0 seconds, for example, 30 seconds, 50 seconds, or longer.

VII. Computer System

Any of the computer systems mentioned herein may utilize any suitable number of subsystems. Examples of such subsystems are shown in FIG. 20 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 20 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystems, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at the same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The invention claimed is:

1. A method for sequencing a nucleic acid molecule using a sequencing cell comprising a nanopore in a membrane that resides over a well, a first electrode at a bottom of the well, a second electrode in a chamber above the membrane, and an electrolyte in the well and the chamber, wherein the first electrode is configured to facilitate non-Faradaic conduction of ionic current and forms a capacitance with ions in the electrolyte, the method comprising:

applying a first voltage signal across the first electrode and the second electrode during a first time period, thereby creating a force that moves the nucleic acid molecule in the sequencing cell through the nanopore, wherein the first voltage signal is configured to increase at a first rate that compensates for a change in the capacitance at the first electrode during application of the first voltage signal such that an effective voltage across the nanopore during the application of the first voltage signal is more level than an effective voltage across the nanopore when the first voltage signal is held constant; and determining a first set of signal values measured during the first voltage signal, the first set of signal values corresponding to one or more nucleotides in the nucleic acid molecule.

2. The method of claim 1, further comprising applying a second voltage signal across the first electrode and the second electrode, the second voltage signal having an opposite polarity as the first voltage signal.

3. The method of claim 1, wherein the nucleic acid molecule has one or more speed bumps that are configured to modify a speed with which the nucleic acid molecule moves through the nanopore to allow measurement of signal values corresponding to one or more nucleotides in the nucleic acid molecule.

4. The method of claim 1, further comprising determining the first rate from a discharging characteristic of the sequencing cell, optionally comprising an RC (Resistance-Capacitance) time constant.

5. The method of claim 1, wherein the first voltage signal is characterized by a linearly increasing magnitude, an exponentially increasing magnitude, or a stepwise signal with increasing magnitude.

6. The method of claim 1, further comprising:

monitoring a nanopore voltage across the nanopore relative to a preset reference voltage; upon detecting a magnitude of the nanopore voltage falling below the preset reference voltage, increasing the magnitude of the first voltage signal to a second voltage higher than the preset reference voltage; and determining a second set of signal values measured during the first voltage signal, the second set of signal values corresponding to one or more nucleotides in the nucleic acid molecule.

7. The method of claim 6, further comprises monitoring a current flowing through the sequencing cell.

8. The method of claim 1, wherein the first voltage signal comprises a plurality of voltage pulse signals superimposed over a base voltage.

9. The method of claim 1, wherein the first set of signal values comprise voltage signals.

10. The method of claim 1, wherein the first set of signal values comprise current signals.

11. A method for sequencing a nucleic acid molecule using a sequencing cell comprising a nanopore in a membrane that resides over a well, a first electrode at a bottom of the well, a second electrode in a chamber above the membrane, and an electrolyte in the well and the chamber, the method comprising:

applying a first voltage signal across the first electrode and the second electrode, wherein the first electrode and the electrolyte are selected to operate in a non-Faradaic manner, thereby creating a force that moves the nucleic acid molecule in the sequencing cell through the nanopore;

determining a first set of one or more signal values measured during the first voltage signal, the first set of one or more signal values corresponding to one or more nucleotides in the nucleic acid molecule;

monitoring a magnitude of nanopore voltage across the nanopore relative to a preset reference voltage;

upon determining that the magnitude of the nanopore voltage is below the preset reference voltage, increasing the magnitude of the first voltage signal to a second voltage such that the nanopore voltage is equal to or higher than the preset reference voltage; and determining a second set of one or more signal values measured during the first voltage signal being at the second voltage, the second set of one or more signal values corresponding to one or more nucleotides in the nucleic acid molecule.

12. The method of claim 11, further comprises monitoring a current flowing through the sequencing cell.

13. The method of claim 11, wherein the first electrode is configured to facilitate non-Faradaic conduction of ionic current and forms a capacitance with ions in the electrolyte.

* * * * *